US010806394B2

(12) United States Patent
Michimori et al.

(10) Patent No.: US 10,806,394 B2
(45) Date of Patent: Oct. 20, 2020

(54) INFORMATION PROCESSING METHOD AND INFORMATION PROCESSING SYSTEM

(71) Applicant: PANASONIC INTELLECTUAL PROPERTY MANAGEMENT CO., LTD., Osaka (JP)

(72) Inventors: Akihiro Michimori, Hyogo (JP); Hiroko Sugimoto, Kyoto (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/799,050

(22) Filed: Feb. 24, 2020

(65) Prior Publication Data
US 2020/0268309 A1 Aug. 27, 2020

(30) Foreign Application Priority Data

Feb. 26, 2019 (JP) ................. 2019-033142
Oct. 7, 2019 (JP) ................. 2019-184638

(51) Int. Cl.
H05B 37/02 (2006.01)
A61B 5/00 (2006.01)
G06F 9/54 (2006.01)
H04L 12/28 (2006.01)
G06N 7/00 (2006.01)

(52) U.S. Cl.
CPC ............ A61B 5/4806 (2013.01); G06F 9/542 (2013.01); G06N 7/005 (2013.01); H04L 12/2827 (2013.01); H04L 2012/2849 (2013.01)

(58) Field of Classification Search
None
See application file for complete search history.

(56) References Cited

U.S. PATENT DOCUMENTS

2011/0275960 A1 11/2011 Westerink
2013/0338446 A1 12/2013 Van Vugt et al.
(Continued)

FOREIGN PATENT DOCUMENTS

JP H04-053527 2/1992
JP 5654489 1/2015

OTHER PUBLICATIONS

Extended European Search Report issued in European Patent Application No. 20158761.5, dated May 13, 2020.

Primary Examiner — Brent Swarthout
(74) Attorney, Agent, or Firm — Greenblum & Bernstein, P.L.C.

(57) ABSTRACT

In an information processing method, a computer acquires a sleep state of a person existing in space, acquires detection data output from a sensor that detects entry of an object into the space, performs a first determination to determine whether or not the sleep state changes to awakening within a predetermined time from a time point at which the object is estimated to enter the space based on the sleep state and the detection data, generates, in association with the sleep state before the time point, awakening information for determining possibility that the person is awakened by entry of the object in a case where the person is in the sleep state before the time point of entry based on a result of the first determination, and presents the awakening information associated with the sleep state via a presentation device.

17 Claims, 31 Drawing Sheets

(56) References Cited

U.S. PATENT DOCUMENTS

| | | | |
|---|---|---|---|
| 2015/0238137 A1* | 8/2015 | Eyal | A61B 5/4815 600/508 |
| 2016/0058429 A1* | 3/2016 | Shinar | A61B 5/02405 600/551 |
| 2018/0132336 A1* | 5/2018 | Chraibi | H05B 47/19 |
| 2018/0353131 A1* | 12/2018 | Winter | A61B 5/4812 |

* cited by examiner

FIG.4

|  | REM SLEEP | LIGHT SLEEP | DEEP SLEEP |
|---|---|---|---|
| AWAKENING PROBABILITY | 0.25(5/20) | 0.5(4/8) | 0.04(1/25) |
| NUMBER OF TIMES OF ENTRY | 20 | 8 | 25 |
| NUMBER OF TIMES OF AWAKENING | 5 | 4 | 1 |

FIG.9

| TRANSITION OF SLEEP STATE OF SLEEPER AFTER PERSON ENTERS BEDROOM | SCORE |
|---|---|
| CASE WHERE SLEEP STATE OF SLEEPER DOES NOT CHANGE TO AWAKE STATE WITHIN PREDETERMINED TIME AFTER PERSON ENTERS BEDROOM | 0 |
| CASE WHERE SLEEP STATE OF SLEEPER CHANGES TO AWAKE STATE WITHIN PREDETERMINED TIME AFTER PERSON ENTERS BEDROOM, AND TRANSITION IS MADE FROM AWAKE STATE TO REM SLEEP STATE, LIGHT SLEEP STATE, OR DEEP SLEEP STATE WITHIN 1 MINUTE | 0.25 |
| CASE WHERE SLEEP STATE OF SLEEPER CHANGES TO AWAKE STATE WITHIN PREDETERMINED TIME AFTER PERSON ENTERS BEDROOM, AND TRANSITION IS MADE FROM AWAKE STATE TO REM SLEEP STATE, LIGHT SLEEP STATE, OR DEEP SLEEP STATE WITHIN TWO MINUTES | 0.50 |
| CASE WHERE SLEEP STATE OF SLEEPER CHANGES TO AWAKE STATE WITHIN PREDETERMINED TIME AFTER PERSON ENTERS BEDROOM, AND TRANSITION IS MADE FROM AWAKE STATE TO REM SLEEP STATE, LIGHT SLEEP STATE, OR DEEP SLEEP STATE WITHIN THREE MINUTES | 0.75 |
| CASE WHERE SLEEP STATE OF SLEEPER CHANGES TO AWAKE STATE WITHIN PREDETERMINED TIME AFTER PERSON ENTERS BEDROOM, AND AWAKE STATE CONTINUES THREE MINUTES OR MORE OR SLEEPER LEAVES BED WITHIN THREE MINUTES | 1.0 |

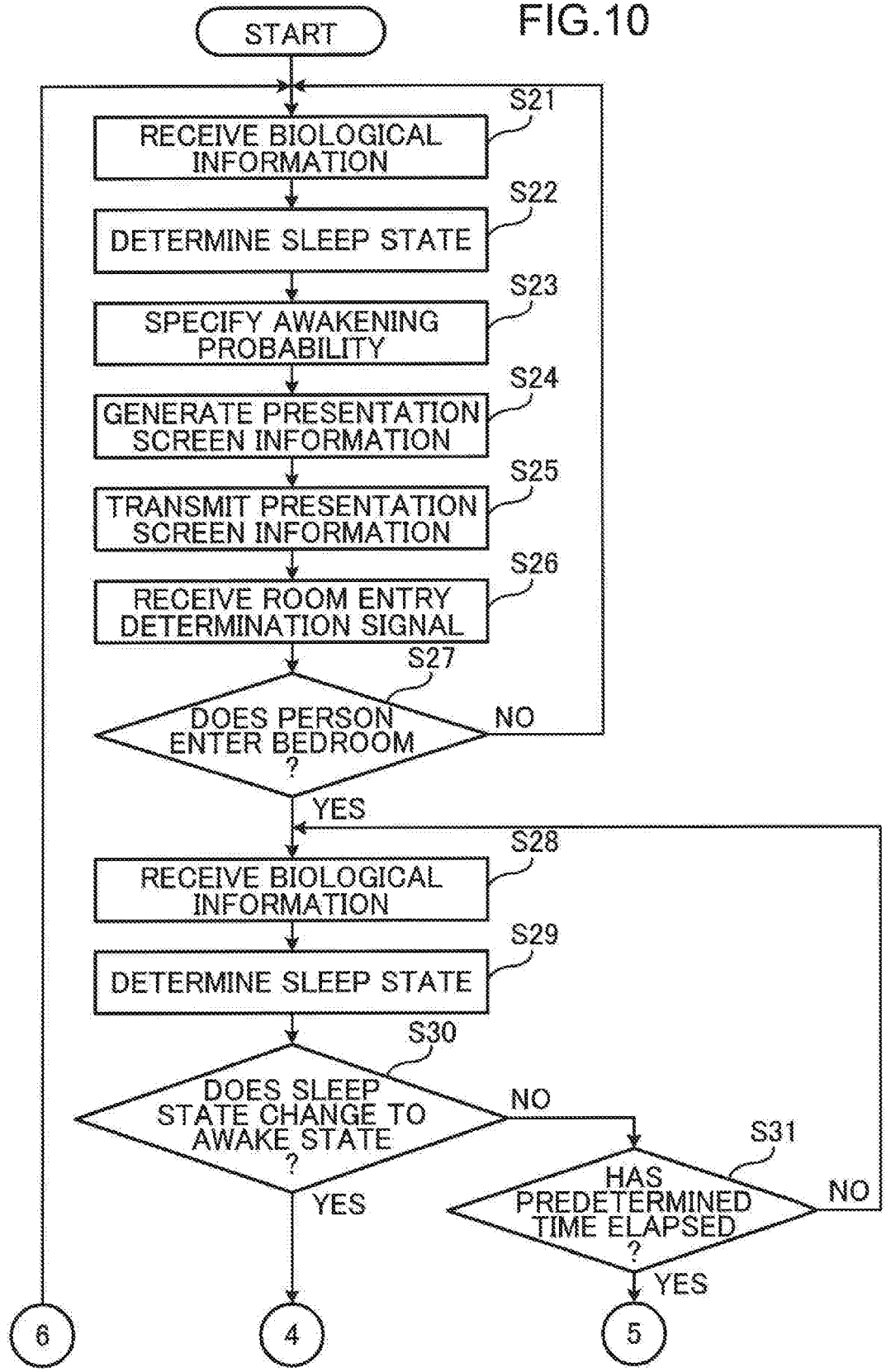

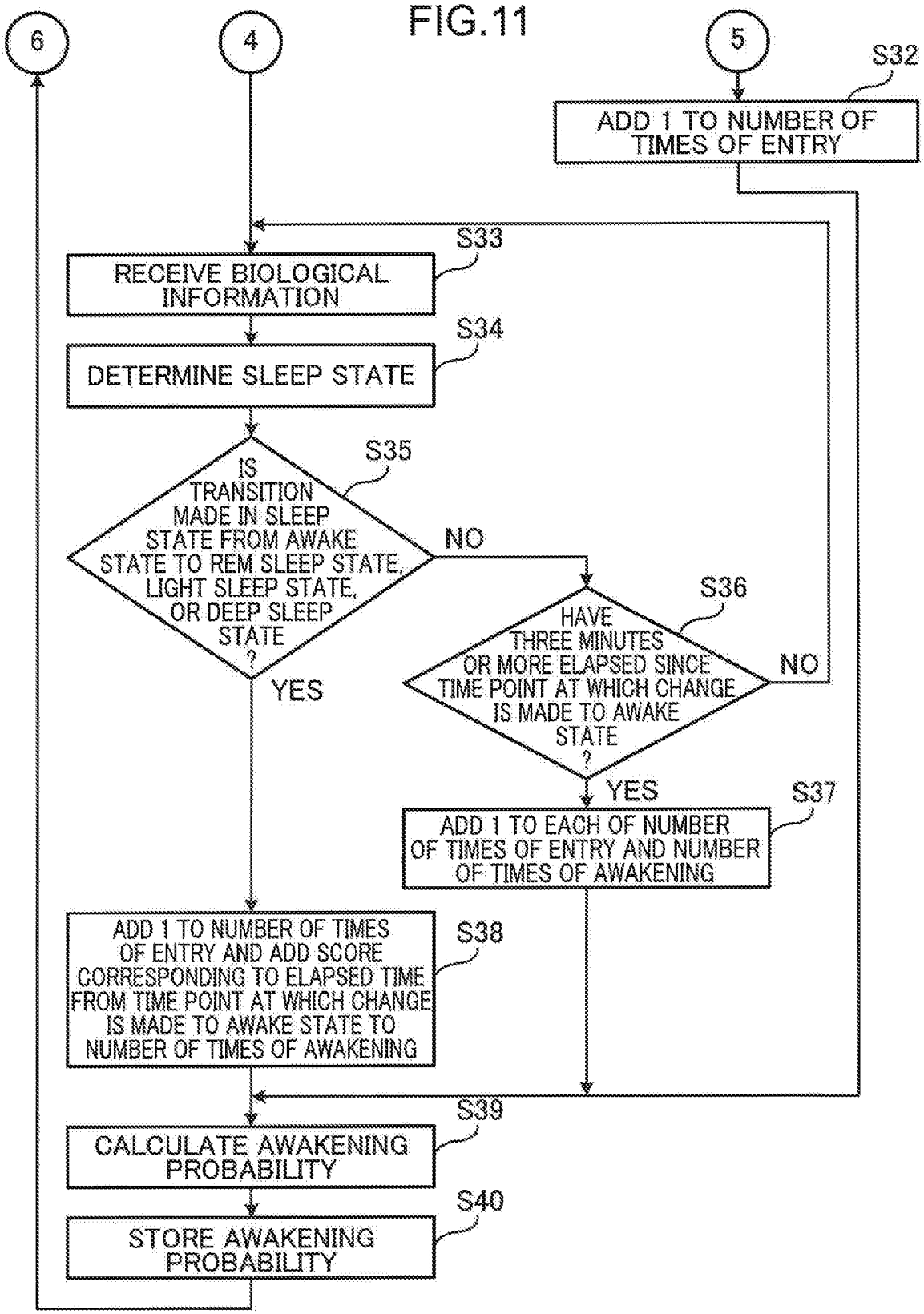

FIG.14

FIRST SLEEPER

|  | REM SLEEP | LIGHT SLEEP | DEEP SLEEP |
|---|---|---|---|
| AWAKENING PROBABILITY | 0.25(5/20) | 0.5(4/8) | 0.04(1/25) |
| NUMBER OF TIMES OF ENTRY | 20 | 8 | 25 |
| NUMBER OF TIMES OF AWAKENING | 5 | 4 | 1 |

SECOND SLEEPER

|  | REM SLEEP | LIGHT SLEEP | DEEP SLEEP |
|---|---|---|---|
| AWAKENING PROBABILITY | 0.3(6/20) | 0.8(8/10) | 0.08(2/25) |
| NUMBER OF TIMES OF ENTRY | 20 | 10 | 25 |
| NUMBER OF TIMES OF AWAKENING | 6 | 8 | 2 |

FIG.19

YAMADA IN BEDROOM IS IN LIGHT SLEEP STATE.
IF YOU ENTER THE ROOM NOW, PROBABILITY OF
AWAKENING YAMADA IS 50%.
PLEASE DO NOT ENTER THE ROOM.

FIG.20

YAMADA IN BEDROOM IS IN DEEP SLEEP STATE.
IF YOU ENTER THE ROOM NOW, PROBABILITY OF
AWAKENING YAMADA IS 4%.
PLEASE OPEN AND CLOSE DOOR AS QUIETLY AS
POSSIBLE TO ENTER THE ROOM.

FIG.27

YAMADA IN BEDROOM IS IN REM SLEEP STATE.
IF YOU ENTER THE ROOM NOW, PROBABILITY
OF AWAKENING YAMADA IS 25%.
SOUND LOWER THAN 40 dB IS RECOMMENDED.

FIG.28

YAMADA IN BEDROOM IS IN REM SLEEP STATE.
IF YOU ENTER ROOM NOW,
YAMADA WILL NOT BE AWAKENED BY BRIGHTNESS
OF 0 TO 10 lux.
PROBABILITY OF AWAKENING YAMADA IS 11%
WITH BRIGHTNESS OF 50 lux.
PROBABILITY OF AWAKENING YAMADA IS 33%
WITH BRIGHTNESS OF 100 lux.
PROBABILITY OF AWAKENING YAMADA IS 71%
WITH BRIGHTNESS OF 300 lux.
PROBABILITY OF AWAKENING YAMADA IS 91%
WITH BRIGHTNESS OF 500 lux.

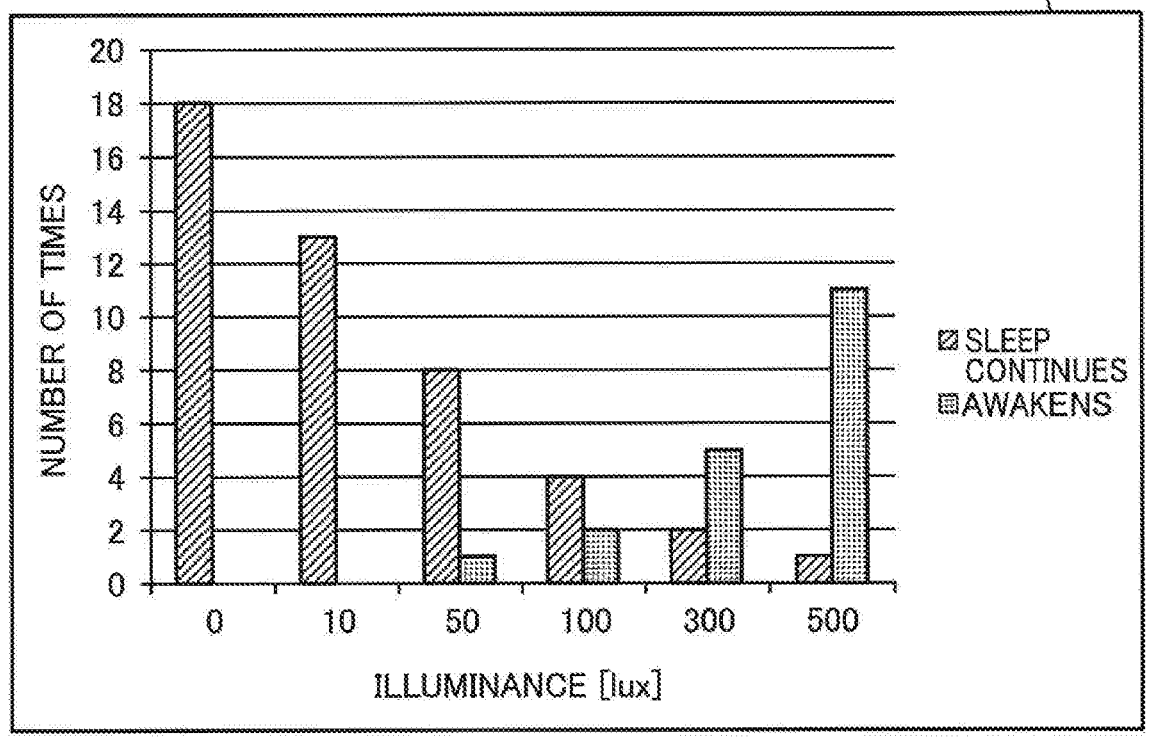

FIG.32

YAMADA IN BEDROOM IS IN REM SLEEP STATE.
IF YOU ENTER THE ROOM NOW, PROBABILITY OF
AWAKENING YAMADA IS 25%.
CEILING LIGHT IS SET TO BE LOWER THAN 100 lux. ~42

FIG.33

YAMADA IN BEDROOM IS IN REM SLEEP STATE.
IF YOU ENTER THE ROOM NOW, PROBABILITY OF
AWAKENING YAMADA IS 25%.
DO YOU SET CEILING LIGHT TO BE
LOWER THAN 100 lux?
YES    NO ~42

FIG.34

YAMADA IN BEDROOM IS IN REM SLEEP STATE.
IF YOU ENTER THE ROOM NOW, PROBABILITY OF
AWAKENING YAMADA IS 25%.
SETTING CEILING LIGHT TO BE
LOWER THAN 100 lux IS RECOMMENDED. ~42

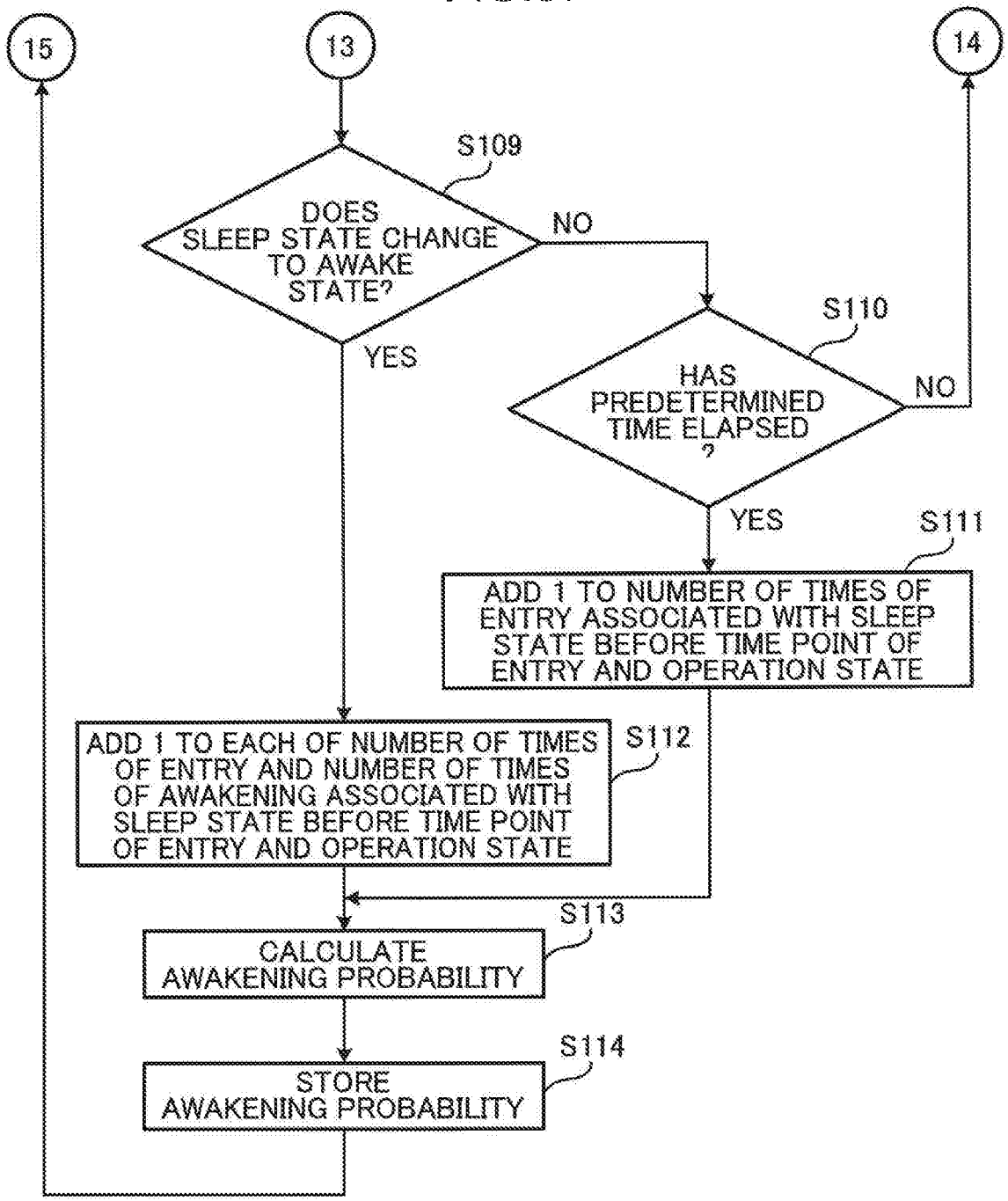

INFORMATION PROCESSING METHOD AND INFORMATION PROCESSING SYSTEM

FIELD OF THE INVENTION

The present disclosure relates to an information processing method and an information processing system which present information according to a sleep state of a person existing in space.

BACKGROUND ART

For a human, sleep is essential for health. Awakening a sleeping human by an environmental stimulus of sound or light may cause discomfort to the sleeping human and may affect a health condition of the sleeping human. For example, when a husband enters a bedroom where a wife is sleeping from outside the bedroom, the wife may awaken due to opening and closing sounds of the door, which may adversely affect sleep of the wife. Further, for example, in a case where a husband enters a bedroom from the outside while his wife is putting an infant to sleep in the bedroom, the infant may awaken due to opening and closing sounds of the door, which may adversely affect sleep of the infant.

For example, Japanese Patent No. 5654489 discloses a room entry information system that detects a sleep stage of a sleeper in a bedroom, issues a room entry instruction for prohibiting entry into the bedroom during a light sleep phase of the sleeper, and issues a room entry instruction for permitting quiet entry into the bedroom during a REM or deep sleep phase of the sleeper.

However, it is difficult to control entry of an object into space where a sleeper is present in accordance with the ease of awakening of each sleeper with the above conventional technique.

SUMMARY OF THE INVENTION

The present disclosure has been made to solve the above problem, and an object of the present disclosure is to provide an information processing method and an information processing system capable of controlling entry of an object into space where a sleeper exists according to ease of awakening of each sleeper.

In an information processing method according to an aspect of the present disclosure, a computer acquires a sleep state of a person existing in space, acquires detection data output from a sensor that detects entry of an object into the space, performs a first determination to determine whether or not the sleep state changes to awakening within a predetermined time from a time point at which the object is estimated to enter the space based on the sleep state and the detection data, generates, in association with the sleep state before the time point, awakening information for determining possibility that the person is awakened by entry of the object in a case where the person is in the sleep state before the time point of entry based on a result of the first determination, and presents the awakening information associated with the sleep state via a presentation device.

BRIEF DESCRIPTION OF THE DRAWINGS

FIG. 4 is a diagram showing an example of awakening information stored in an awakening information storage unit in the first embodiment;

FIG. 9 is a diagram showing an example of a state transition table stored in a state transition table storage unit in the second embodiment;

FIG. 10 is a first flowchart for describing operation of the server apparatus in the second embodiment of the present disclosure;

FIG. 11 is a second flowchart for describing operation of the server apparatus in the second embodiment of the present disclosure;

FIG. 14 is a diagram showing an example of awakening information stored in the awakening information storage unit in the third embodiment;

FIG. 19 is a diagram showing an example of room entry suppression screen information displayed on the display device in the fourth embodiment;

FIG. 20 is a diagram showing an example of room entry permission screen information displayed on the display device in the fourth embodiment;

FIG. 27 is a diagram showing a second variation of presentation screen information displayed on the display device in the fifth embodiment;

FIG. 28 is a diagram showing a third variation of presentation screen information displayed on the display device in the fifth embodiment;

FIG. 29 is a diagram showing a fourth variation of presentation screen information displayed on the display device in the fifth embodiment;

FIG. 30 is a diagram showing a fifth variation of presentation screen information displayed on the display device in the fifth embodiment;

FIG. 32 is a diagram showing an example of presentation screen information displayed on the display device in the sixth embodiment of the present disclosure;

FIG. 33 is a diagram showing a first variation of presentation screen information displayed on the display device in the sixth embodiment of the present disclosure;

FIG. 34 is a diagram showing a second variation of presentation screen information displayed on the display device in the sixth embodiment of the present disclosure;

FIG. 37 is a second flowchart for describing operation of the server apparatus in the seventh embodiment of the present disclosure.

Figure 1:
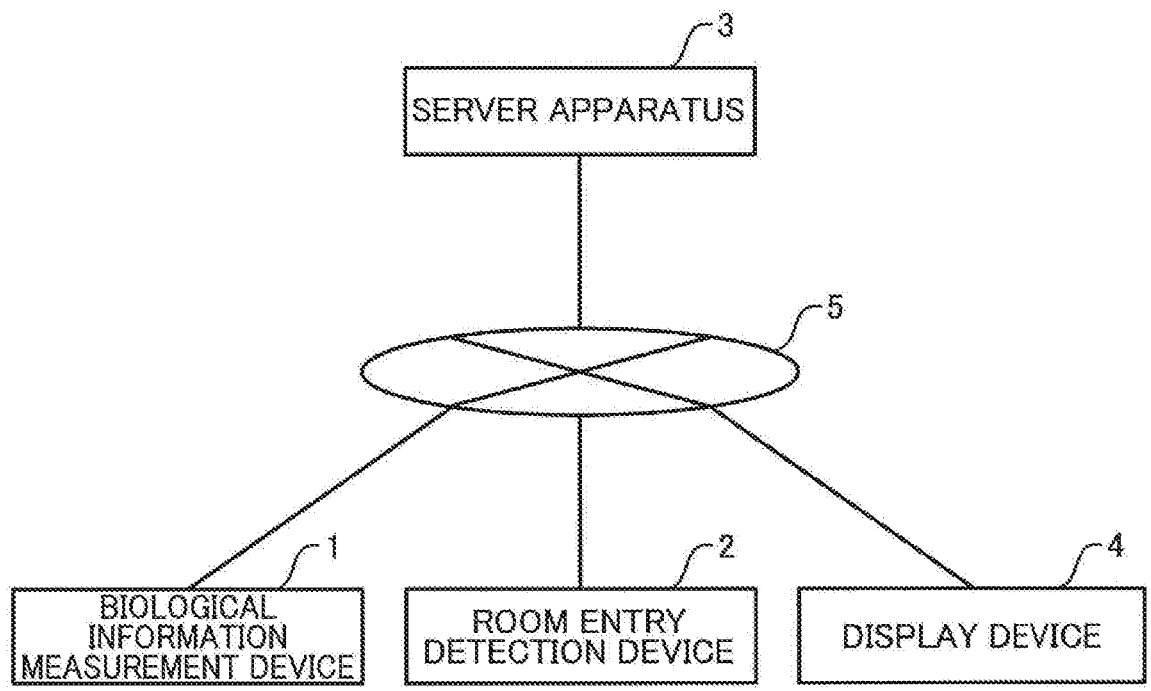
FIG. 1 is a diagram showing an entire configuration of an information presentation system in a first embodiment.

DESCRIPTION OF EMBODIMENTS (Knowledge that Forms the Basis of the Present Disclosure)

It is known that, when a human goes to sleep, transition is first made from an awake state to a light sleep state (stage-1 or stage-2 non-REM sleep state), and then the light sleep state, a deep sleep state (stage-3 or stage-4 non-REM sleep state), and a REM sleep state are repeated in a cycle of 90 to 120 minutes. A human is considered to be likely to awaken when a sound or light environmental stimulus is given during a light sleep state, and to be less likely to awaken even when a sound or light environmental stimulus is given during a deep sleep state or a REM sleep state.

The ease of awakening of a sleeper in response to a sound or light environmental change caused by a person entering a bedroom is different from individual to individual. That is, among sleepers, there is a sleeper who is awakened by a slight environmental change even in a deep sleep state, or sleeper who is less likely to be awakened by an environmental change, such as opening and closing sounds of a door, even in a light sleep state.

For example, in the room entry information system disclosed in Japanese Patent No. 5654489, in a case where a sleeper is a person who is easily awakened, the sleeper may be awakened by an environmental change caused by a person entering a room even if a sleep state of the sleeper is a deep sleep state.

In order to solve the above problem, according to an aspect of the present disclosure, there is provided an information processing method executed by a computer. The information processing method includes acquiring a sleep state of a person existing in space, acquiring detection data output from a sensor that detects entry of an object into the space, performing a first determination to determine whether or not the sleep state changes to awakening within a predetermined time from a time point at which the object is estimated to enter the space based on the sleep state and the detection data, generating, in association with the sleep state before the time point, awakening information for determining possibility that the person is awakened by entry of the object in a case where the person is in the sleep state before the time point based on a result of the first determination, and presenting the awakening information associated with the sleep state via a presentation device.

According to the above configuration, the awakening information for determining the possibility of a person awakened by the entry of an object in a case where the person is in the sleep state before the time point of entry at which an object is estimated to enter space is generated in association with the sleep state before the time point of entry, and the awakening information associated with the sleep state is presented via the presentation device. Accordingly, entry of an object into space where the sleeper is present can be controlled according to the ease of awakening of each sleeper. As a result, the risk of awakening a sleeper even in space where an object may enter can be reduced. Further, an object can be caused to enter the space without awakening the sleeper.

In the above information processing method, the presenting the awakening information may include presenting the awakening information in a case where the sleep state is not awakening.

According to this configuration, the awakening information is not presented in a case where the sleep state of the sleeper is awakening, so that unnecessary awakening information can be prevented from being presented.

Further, the above information processing method may further include performing a second determination to determine transition of a sleep state after the sleep state changes to awakening based on the sleep state, in which the generating the awakening information includes generating the awakening information based on a result of the first determination and a result of the second determination.

According to this configuration, different pieces of the awakening information can be presented for a person who is likely to fall asleep even after being awakened and a person who is unlikely to fall asleep once being awakened. Therefore, the entry of an object can be controlled according to the sleep state after awakening of an individual person.

Further, in the above information processing method, the generating the awakening information may include generating the awakening information based on whether or not transition is determined to be made in the sleep state from awakening to another state in the second determination.

According to this configuration, different pieces of the awakening information can be presented for a case where transition is determined to be made in the sleep state from awakening to another state, that is, a case where the person in the space falls asleep soon after being awakened, and a case where transition is determined not to be made in the sleep state from awakening to another state, that is, a case where the person in the space is awake continuously.

Further, in the above information processing method, the generating the awakening information may include generating the awakening information based on an elapsed time from a time point at which the sleep state changes to awakening to a time point at which transition is determined to be made in the sleep state from awakening to the another state in the second determination.

According to this configuration, the awakening information is generated based on an elapsed time from a time point at which the sleep state changes to awakening to a time point transition is determined to be made in the sleep state from awakening to another state in the second determination. Accordingly, the entry of an object into the space where the sleeper is present can be controlled in accordance with the ease of falling asleep of each sleeper after being awakened.

Further, in the above information processing method, the generating the awakening information may include calculating possibility of awakening of the person based on a result of the first determination, and generating the calculated possibility of awakening as the awakening information.

According to this configuration, since the possibility that a person is awakened is generated as the awakening information, for example, a person who is going to enter the space can predict whether or not a sleeper in the space is awakened by viewing the awakening information.

Further, the above information processing method may further include acquiring sound data output from a microphone existing in the space, and determining a characteristic of a sound within the space within a predetermined time from a time point at which the object is estimated to enter the space based on the sound data and the detection data, in which the generating the awakening information may include associating the determined characteristic of the sound with the awakening information, and the presenting the awakening information may include presenting the awakening information and the characteristic of the sound associated with the awakening information.

According to this configuration, a characteristic of a sound in the space within a predetermined time from a time point at which the object is estimated to enter the space is associated with the awakening information, and the awakening information and the characteristic of the sound associated with the awakening information are presented. Accordingly, the entry of the object into the space where the sleeper is present can be controlled in accordance with the ease of awakening of the individual sleeper with respect to the characteristic of the sound generated when the object enters the space.

Further, in the information processing method, the presenting the awakening information may include presenting the awakening information corresponding to the characteristic of the sound.

According to this configuration, since the awakening information is presented corresponding to the characteristic of the sound, how much the sound generated when the object enters the space has an influence on the awakening of the sleeper can be notified.

Further, in the above information processing method, the presenting the awakening information may include presenting information based on the characteristic of the sound associated with the awakening information to be presented.

According to this configuration, information based on the characteristic of the sound associated with the awakening information to be presented is presented. Accordingly, for example, to what degree a sound may be generated can be presented to a person who attempts to enter the space.

Further, the above information processing method may further include acquiring illuminance data output from an illuminance sensor existing in the space, and determining a characteristic of an illuminance within the space within a predetermined time from a time point at which the object is estimated to enter the space based on the illuminance data and the detection data, in which the generating the awakening information may include associating the determined characteristic of the illuminance with the awakening information, and the presenting the awakening information may include presenting the awakening information and the characteristic of the illuminance associated with the awakening information.

According to this configuration, a characteristic of an illuminance in the space within a predetermined time from a time point at which the object is estimated to enter the space is associated with the awakening information, and the awakening information and the characteristic of the illuminance associated with the awakening information are presented. Accordingly, the entry of the object into the space where the sleeper is present can be controlled in accordance with the ease of awakening of the individual sleeper with respect to the characteristic of the illuminance generated when the object enters the space.

Further, in the information processing method, the presenting the awakening information may include presenting the awakening information corresponding to the characteristic of the illuminance.

According to this configuration, since the awakening information is presented corresponding to the characteristic of the illuminance, how much the illumination generated when the object enters the space has an influence on the awakening of the sleeper can be notified.

Further, in the above information processing method, the presenting the awakening information may include presenting information based on the characteristic of the illuminance associated with the awakening information to be presented.

According to this configuration, information based on the characteristic of the illuminance associated with the awakening information to be presented is presented. Accordingly, for example, to what degree the illumination may be generated can be presented to a person who attempts to enter the space.

According to another aspect of the present disclosure, there is provided an information processing system including an information processing device, a sensor that detects entry of an object into space, and a presentation device. The information processing device includes a sleep state acquisition unit that acquires a sleep state of a person existing in the space, a detection data acquisition unit that acquires detection data output from the sensor, a determination unit that performs a first determination to determine whether or not the sleep state changes to awakening within a predetermined time from a time point at which the object is estimated to enter the space based on the sleep state and the detection data, a generation unit that generates, in association with the sleep state before the time point, awakening information for determining possibility that the person is awakened by entry of the object in a case where the person is in the sleep state before the time point based on a result of the first determination, and a presentation unit that presents the awakening information associated with the sleep state via the presentation device.

According to the above configuration, the awakening information for determining the possibility of a person awakened by the entry of an object in a case where the person is in the sleep state before the time point of entry at which an object is estimated to enter space is generated in association with the sleep state before the time point of entry, and the awakening information associated with the sleep state is presented via the presentation device. Accordingly, entry of an object into space where the sleeper is present can be controlled according to the ease of awakening of each sleeper. As a result, the risk of awakening a sleeper even in space where an object may enter can be reduced. Further, an object can be caused to enter the space without awakening the sleeper.

According to another aspect of the present disclosure, there is provided an information processing method executed by a computer, the information processing method including acquiring a sleep state of a person existing in space, acquiring detection data output from a sensor that detects entry of an object into the space, performing a first determination to determine whether or not the sleep state changes to awakening within a predetermined time from a time point at which the object is estimated to enter the space based on the sleep state and the detection data, generating, in association with the sleep state before the time point, awakening information for determining possibility that the person is awakened by entry of the object in a case where the person is in the sleep state before the time point based on a result of the first determination, and executing, based on the awakening information associated with the sleep state, home appliance control processing that is at least one of controlling a home appliance in the space, inquiring whether or not to control the home appliance via a presentation device, and presenting recommendation for controlling the home appliance via the presentation device.

According to this configuration, the home appliance control processing is executed based on the awakening information associated with the sleep state. Therefore, when an object enters the space, a home appliance can be used to control the environment in the space to be an environment in which the sleeper is unlikely to awaken. Therefore, even if an object enters the space, awakening of the sleeper can be suppressed.

Further, the above information processing method may further include presenting the awakening information via the presentation device.

According to this configuration, an object can be caused to enter the space without awakening the sleeper.

Further, the above information processing method may further include acquiring a position of the object, and determining a timing of executing the home appliance control processing or a timing of presenting the awakening information based on a positional relationship between the position of the object and the space.

According to this configuration, unnecessary control and presentation can be reduced as a home appliance is controlled or the presentation information is presented at a timing at which the possibility that an object enters the space becomes high.

Further, the above information processing method may further include acquiring an operation state of the home appliance, generating, in association with the sleep state before the time point and the operation state, awakening information for determining possibility that the person is awakened by entry of the object in a case where the person is in the sleep state before the time point and the operation state based on a result of the first determination, and executing the home appliance control processing based on the awakening information associated with the sleep state and the operation state.

According to this configuration, an environment in which a sleeper is unlikely to awaken when an object enters space can be provided without a sensor for sensing the environment of the space.

Hereinafter, embodiments of the present disclosure will be described with reference to the drawings. Note that all embodiments described below show a comprehensive and specific example. Numerical values, shapes, constituents, steps, order of steps, and the like described in the embodiments below are merely examples, and are not intended to limit the present disclosure. Further, among the constituents in the embodiments below, constituents not described in an independent claim indicating the highest concept are described as optional constituents. Further, in all the embodiments, the content of each can be combined with one another.

First Embodiment

Figure 2:
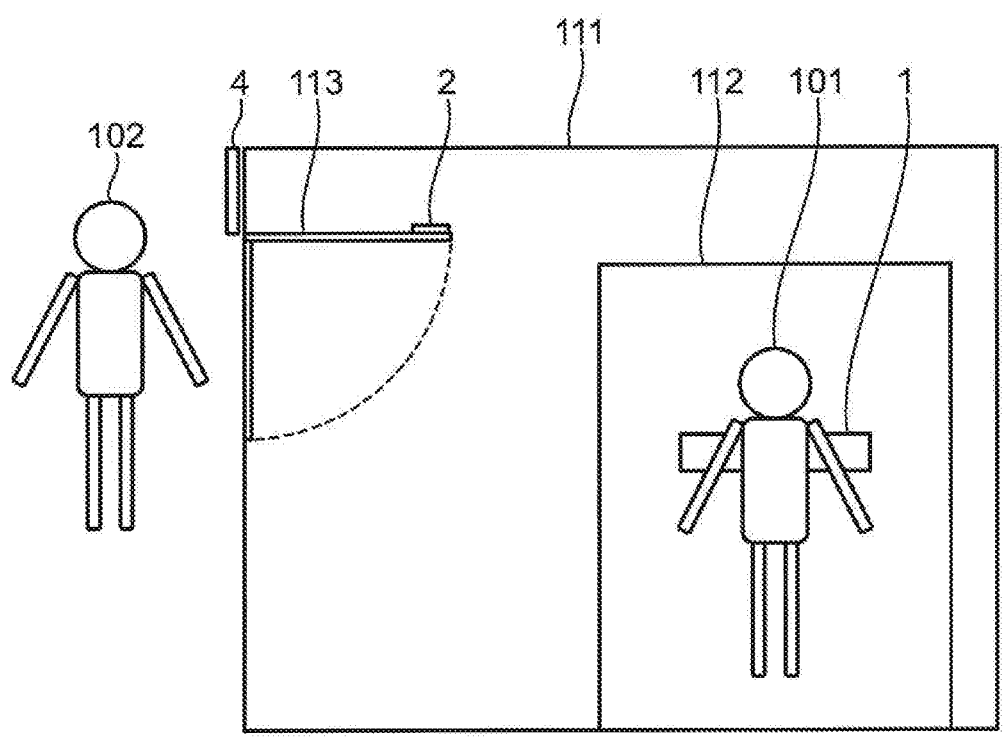
FIG. 2 is a diagram showing an example of a bedroom in which a biological information measurement device, a room entry detection device, and a display device are disposed in the first embodiment.

FIG. 1 is a diagram showing an entire configuration of an information presentation system in a first embodiment, and FIG. 2 is a diagram showing an example of a bedroom in which a biological information measurement device, a room entry detection device, and a display device in the first embodiment.

The information presentation system shown in FIG. 1 includes a biological information measurement device 1, a room entry detection device 2, a server apparatus 3, and a display device 4. The server apparatus 3 is connected to each of the biological information measurement device 1, the room entry detection device 2, and the display device 4 via a network 5 in such a manner that the devices can communicate with each other. The network 5 is, for example, the Internet.

As shown in FIG. 2, a bed mattress 112 on which a sleeper 101 sleeps is disposed in a bedroom 111.

The biological information measurement device 1 is installed, for example, under the bed mattress 112, and measures biological information, such as a heart rate, a respiratory rate, and a body movement amount, of the sleeper 101.

The room entry detection device 2 is disposed on a door 113 provided at an entrance of the bedroom 111, and detects entry of an object into space where the sleeper 101 goes to sleep, that is, the bedroom 111. The room entry detection device 2 detects entry of an entering person 102 entering the bedroom 111.

The display device 4 is disposed on a wall surface on the entrance side of the bedroom 111 and displays information to be presented to the entering person 102.

If the entering person 102 enters the bedroom 111 when the sleeper 101 in the bedroom 111 is sleeping, there is possibility that the sleeper 101 is awakened by opening and closing sounds of the door 113 or light from a lighting device in the bedroom 111. In view of the above, the information presentation system presents awakening information to the entering person 102 for determining the possibility that the sleeper 101 is awakened by entry of the entering person 102.

Figure 3:
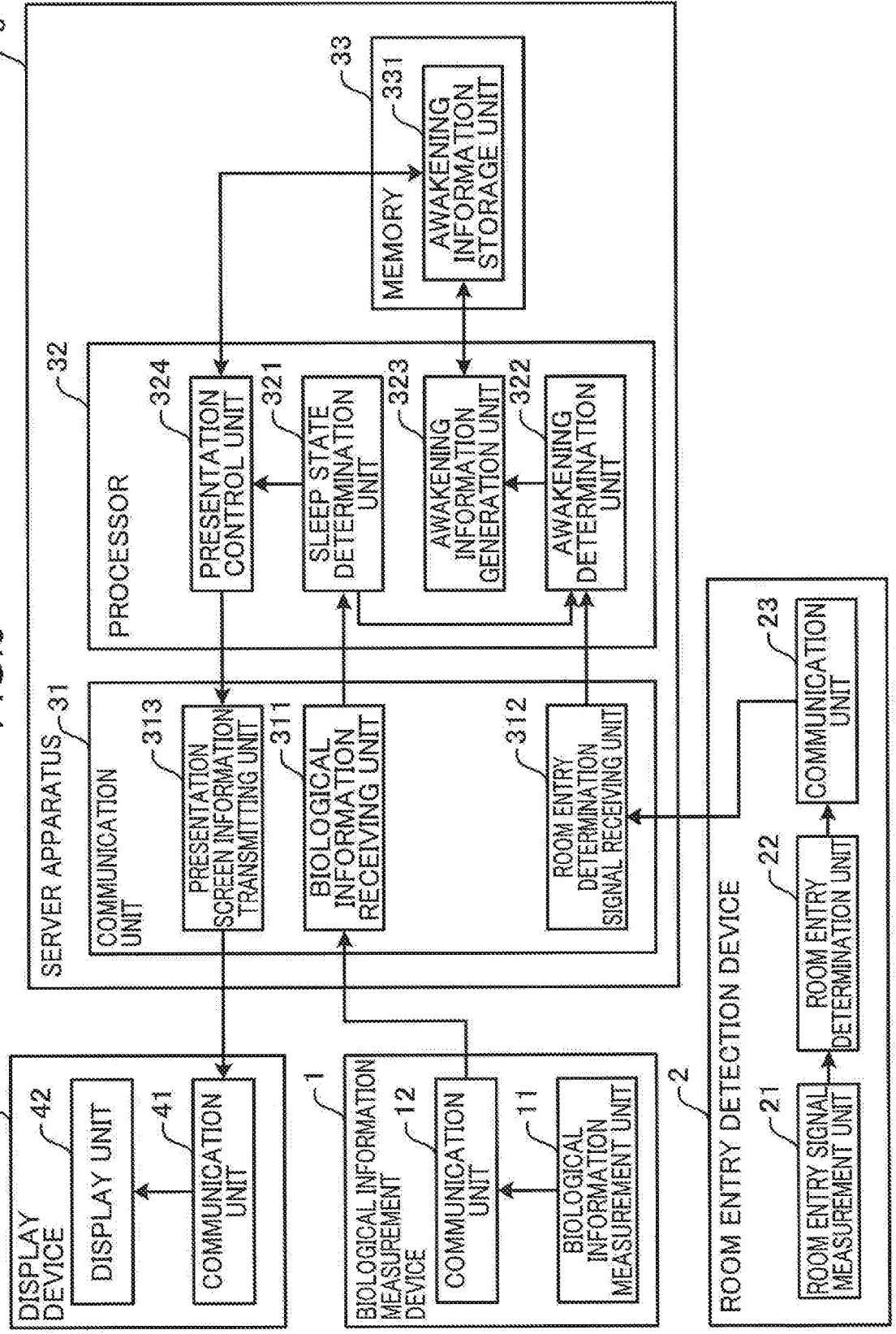
FIG. 3 is a block diagram showing a configuration of an information presentation system in the first embodiment.

FIG. 3 is a block diagram showing a configuration of the information presentation system in the first embodiment.

The biological information measurement device 1 includes a biological information measurement unit 11 and a communication unit 12.

The biological information measurement unit 11 is, for example, a sheet-type piezoelectric sensor installed under the bed mattress 112 where the sleeper 101 goes to sleep, and acquires biological information, such as a heart rate, a respiratory rate, and a body movement amount, of the sleeper 101. The biological information measurement unit 11 acquires biological information of the sleeper 101 periodically (for example, every 10 minutes). The communication unit 12 transmits the biological information acquired by the biological information measurement unit 11 to the server apparatus 3.

Note that the biological information measurement unit 11 is not limited to a piezoelectric sensor, and may be a sensor that acquires biological information by other methods, such as a radio wave sensor. Further, in a case where the sleeper 101 is lying on the bed mattress 112, the biological information measurement unit 11 acquires biological information of the sleeper 101. For this reason, in a case where the sleeper 101 is not lying on the bed mattress 112, the biological information measurement unit 11 does not acquire biological information of the sleeper 101, and the communication unit 12 does not transmit biological information of the sleeper 101 to the server apparatus 3. Whether or not the sleeper 101 leaves the bed mattress 112 can be determined based on the presence or absence of biological information.

The room entry detection device 2 includes a room entry signal measurement unit 21, a room entry determination unit 22, and a communication unit 23.

The room entry signal measurement unit 21 is, for example, an acceleration sensor and is disposed on the door 113 of the bedroom 111. The room entry signal measurement unit 21 measures acceleration of the door 113 and outputs the measured acceleration as a room entry signal. When the door 113 is opened, an acceleration value of the door 113 changes. For this reason, by measuring the acceleration of the door 113, whether or not the door 113 is opened can be determined, and, in a case where the door 113 is opened, a person can be determined to enter the room.

The room entry determination unit 22 uses a room entry signal output from the room entry signal measurement unit 21 to determine whether or not the entering person 102 enters the bedroom 11. The room entry determination unit 22 determines whether or not the acceleration measured by the room entry signal measurement unit 21 is equal to or greater than a threshold. When determining that the acceleration measured by the room entry signal measurement unit 21 is equal to or greater than the threshold, the room entry determination unit 22 determines that the door 113 is opened and the entering person 102 enters the bedroom 111.

The communication unit 23 transmits, to the server apparatus 3, a determination result by the room entry determination unit 22, that is, a room entry determination signal indicating whether or not the entering person 102 enters the bedroom 111.

Note that the room entry signal measurement unit 21 is not limited to an acceleration sensor, and may be a motion sensor disposed in the vicinity of the door 113. The motion sensor detects a person who enters the bedroom 111.

The server apparatus 3 includes a communication unit 31, a processor 32, and a memory 33. The communication unit 31 includes a biological information receiving unit 311, a room entry determination signal receiving unit 312, and a presentation screen information transmitting unit 313. The processor 32 includes a sleep state determination unit 321, an awakening determination unit 322, an awakening information generation unit 323, and a presentation control unit 324. The memory 33 includes an awakening information storage unit 331.

The biological information receiving unit 311 receives biological information transmitted by the biological information measurement device 1. The biological information receiving unit 311 outputs the received biological information to the sleep state determination unit 321.

The room entry determination signal receiving unit 312 receives a room entry determination signal transmitted by the room entry detection device 2. The room entry determination signal receiving unit 312 acquires a room entry determination signal (detection data) output from the room entry detection device 2 (sensor) that detects entrance of a person (object) into the bedroom 111 (space). The room entry determination signal receiving unit 312 outputs the received room entry determination signal to the awakening determination unit 322.

The sleep state determination unit 321 determines a sleep state of the sleeper 101 based on the biological information of the sleeper 101 received by the biological information receiving unit 311. The sleep state determination unit 321 acquires a sleep state of a person existing in the bedroom 111 (space).

A person's sleep can be classified into a plurality of sleep states that change in time series according to a depth of sleep or a characteristic of sleep. Generally, sleep is classified into REM sleep and non-REM sleep. REM sleep is sleep with a rapid eye movement. In REM sleep, the body is in a rest state, while the brain is in an active state. A person is considered to have a dream during REM sleep in many cases. Non-REM sleep is sleep that does not involve a rapid eye movement, and is further divided into four stages, stage 1 to stage 4, depending on the depth of sleep. Stage 4 is the deepest sleep level. Non-REM sleep normally reaches stage 3 or stage 4 within 45 to 60 minutes after falling asleep, and then the sleep gradually becomes light and enters REM sleep in about one to two hours. Thereafter, non-REM sleep and REM sleep are considered to be repeated alternately in a sleep cycle of 90 to 110 minutes, which varies from individual to individual, or within an individual.

Biological information of a body movement amount, a respiratory rate, and a heart rate has a correlation with a sleep state. For example, in deep a sleep state, such as stage 3 or stage 4 of non-REM sleep, it is known that a body movement amount is small and a heart rate variability (RRI) is low. The sleep state determination unit 321 estimates a sleep state of a sleeper in real time from the biological information using such a correlation. The sleep state determination unit 321 estimates which state of awakening, REM sleep, stage-1 non-REM sleep, stage-2 non-REM sleep, stage-3 non-REM sleep, and stage-4 non-REM sleep the user is in, based on the biological information.

In the first embodiment, the sleep state includes an awake state, a REM sleep state, a light sleep state, and a deep sleep state. The awake state is a state in which the subject is awake. The REM sleep state is a state in which the subject is in REM sleep. The light sleep state is a state in which the subject is in stage-1 non-REM sleep or stage-2 non-REM sleep. The deep sleep state is a state in which the subject is in stage-3 non-REM sleep or stage-4 non-REM sleep. The sleep state determination unit 321 determines which of the awake state, the REM sleep state, the light sleep state, and the deep sleep state a sleep state of the sleeper 101 is in.

Note that, in the first embodiment, stage-1 non-REM sleep or stage-2 non-REM sleep corresponds to the light sleep state, and stage-3 non-REM sleep or stage-4 non-REM sleep corresponds to the deep sleep state. However, the present disclosure is not particularly limited to this. Stage-1 non-REM sleep may correspond to a light sleep state, and stage-2 non-REM sleep, stage-3 non-REM sleep, or stage-4 non-REM sleep may correspond to a deep sleep state. Further, stage-1 non-REM sleep, stage-2 non-REM sleep, and stage-3 non-REM sleep may correspond to a light sleep state, and stage-4 non-REM sleep may correspond to a deep sleep state.

Further, the REM sleep state may be classified as the deep sleep state, and the sleep state determination unit 321 may determine which of the awake state, the light sleep state, and the deep sleep state a sleep state of the sleeper 101 is in.

The awakening determination unit 322 performs first determination to determine whether or not a sleep state is changed to awakening within a predetermined time from a time point of entry, at which a person (object) is estimated to enter the bedroom 111 (space), based on a sleep state and the room entry determination signal (detection data).

Based on a result of the first determination by the awakening determination unit 322, the awakening information generation unit 323 generates, in association with the sleep state before the time point of entry, awakening information for determining the possibility of a person awakened by the entry of a person (object) in a case where the person is in the sleep state before the time point of entry. The awakening information generation unit 323 may calculate the possibility of a person being awakened based on the result of the first determination, and generate the calculated possibility of awakening as the awakening information. Note that the possibility that a person is awakened is, for example, awakening probability.

The awakening information generation unit 323, for example, counts the number of times of entry indicating the number of times another person enters a room while a sleeper is sleeping, and the number of times of awakening indicating the number of times a sleep state of a sleeper changes to awakening within a predetermined time from a time point of entry at which the other person is estimated to enter the bedroom 111, and generates the awakening probability by dividing the number of times of awakening by the number of times of entry in association with the sleep state before the time point of entry.

The awakening information storage unit 331 stores a combination of the number of times of entry and the number of times of awakening and the awakening probability in association with the sleep state before the time point of entry.

FIG. 4 is a diagram showing an example of the awakening information stored in the awakening information storage unit in the first embodiment.

As shown in FIG. 4, the awakening information storage unit 331 stores the number of times of entry, the number of times of awakening, and the awakening probability in association with the sleep state. The awakening information generation unit 323 calculates the awakening probability by dividing the number of times of awakening by the number of times of entry. For example, the awakening probability associated with the REM sleep state is 0.25. This represents that, in a case where an entering person enters the bedroom when a sleeper in the bedroom is in the REM sleep state, the sleeper is awakened with the probability of 0.25 (25%). A higher awakening probability indicates that the sleeper is more likely to awaken, and a lower awakening probability indicates that the sleeper is less likely to awaken. That is, the awakening probability associated with the REM sleep state is 0.25, the awakening probability associated with the light sleep state is 0.5, and the awakening probability associated with the deep sleep state is 0.04. This shows that the sleeper is least likely to awaken in a case of being in the deep sleep state, and the sleeper is most likely to awaken in a case of being in the light sleep state.

The presentation control unit 324 presents the awakening information associated with the sleep state via the display device 4 (presentation device). The presentation control unit 324 refers to the awakening information storage unit 331, specifies the awakening information associated with the sleep state determined by the sleep state determination unit 321, and generates presentation screen information for presenting the specified awakening information. The presentation screen information is information for presenting the sleep state of the sleeper and the awakening probability corresponding to the sleep state.

Note that the presentation control unit 324 preferably presents awakening information in a case where the sleep state is not awakening. That is, in a case where the sleep state is awakening, a person in the bedroom is not sleeping, so that the other person does not wake up the person in the bedroom by entering the bedroom. For this reason, the presentation control unit 324 does not need to present the awakening information in a case where the sleeping state is awakening, and may present the awakening information in a case where the sleeping state is not awakening.

The presentation screen information transmitting unit 313 transmits the presentation screen information generated by the presentation control unit 324 to the display device 4.

The display device 4 includes a communication unit 41 and a display unit 42.

The communication unit 41 receives the presentation screen information transmitted by the server apparatus 3.

The display unit 42 is, for example, a liquid crystal display device, and displays the presentation screen information received by the communication unit 41.

Figure 5:
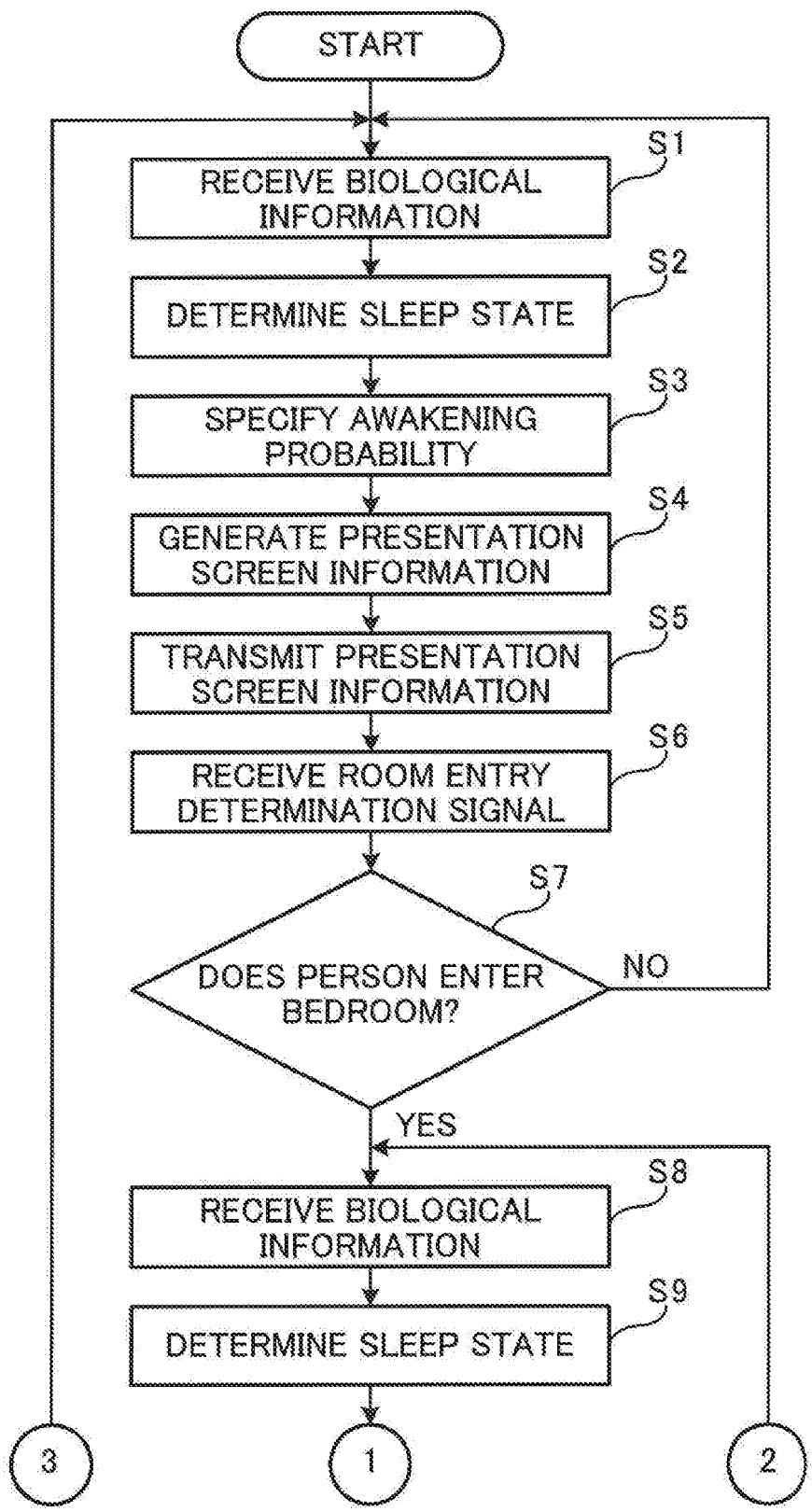
FIG. 5 is a first flowchart for describing operation of a server apparatus in the first embodiment of the present disclosure.
Figure 6:
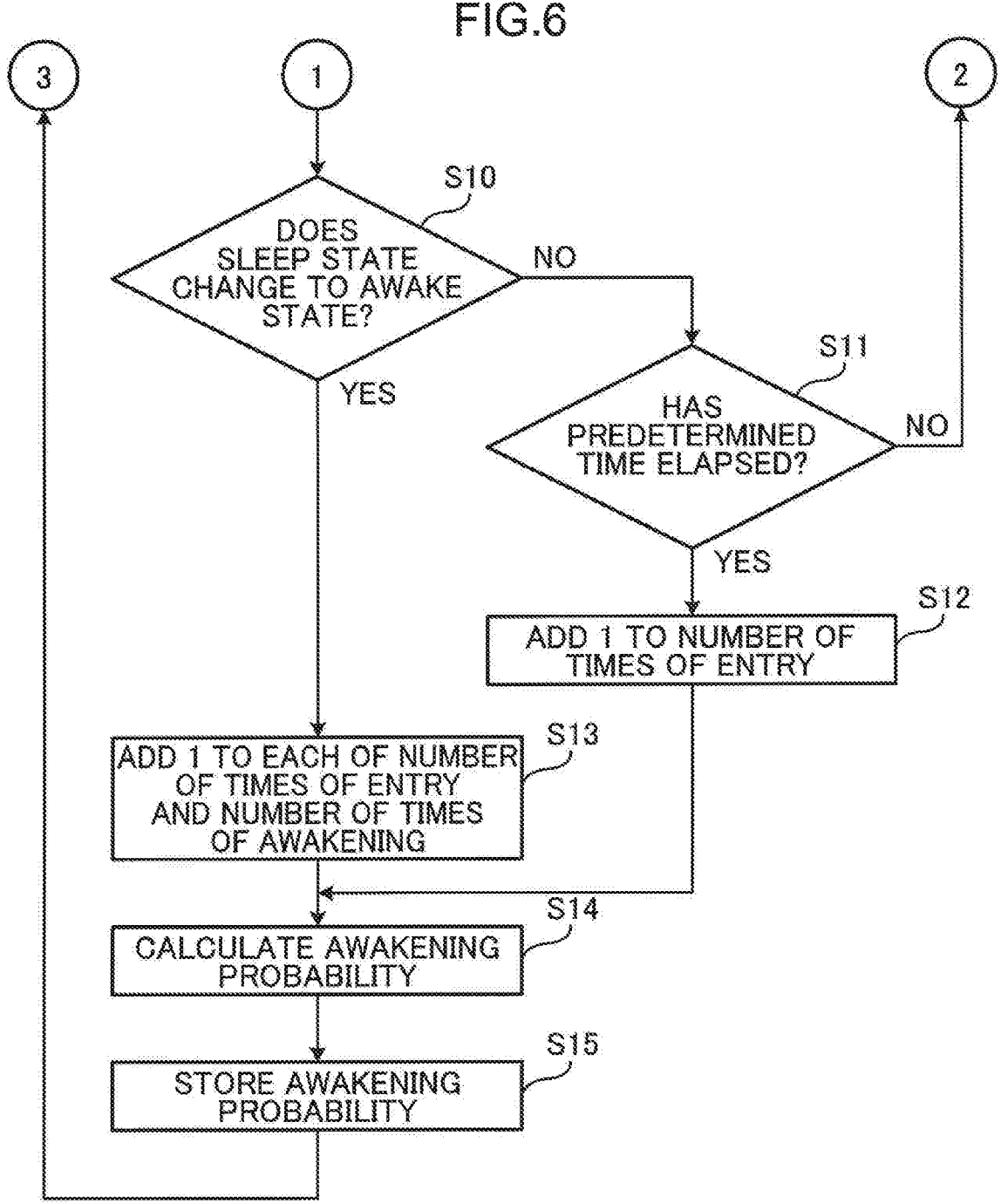
FIG. 6 is a second flowchart for describing operation of the server apparatus in the first embodiment of the present disclosure.

FIG. 5 is a first flowchart for describing operation of the server apparatus according to the first embodiment of the present disclosure. FIG. 6 is a second flowchart for describing the operation of the server apparatus according to the first embodiment of the present disclosure.

First, the biological information receiving unit 311 receives biological information transmitted by the biological information measurement device 1 (step S1).

Next, the sleep state determination unit 321 determines a sleep state of a sleeper based on the biological information of the sleeper received by the biological information receiving unit 311 (step S2). Note that, in a case where the sleep state of the sleeper is determined to be the awake state, the processing may return to step S1. Then, the processing of step S1 and step S2 may be performed repeatedly until the sleep state of the sleeper is determined to be any one of the REM sleep state, the light sleep state, and the deep sleep state.

Next, the presentation control unit 324 refers to the awakening information storage unit 331 to specify the awakening probability associated with the sleep state determined by the sleep state determination unit 321 (step S3).

Next, the presentation control unit 324 generates presentation screen information for presenting the specified awakening probability (step S4).

Next, the presentation screen information transmitting unit 313 transmits the presentation screen information generated by the presentation control unit 324 to the display device 4 (step S5). The communication unit 41 of the display device 4 receives the presentation screen information transmitted by the server apparatus 3. The display unit 42 displays the presentation screen information received by the communication unit 41.

Figure 7:
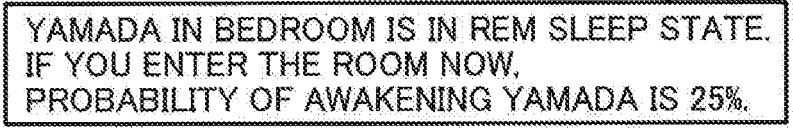
FIG. 7 is a diagram showing an example of presentation screen information displayed on the display device in the first embodiment.

FIG. 7 is a diagram showing an example of presentation screen information displayed on the display device in the first embodiment.

In a case where the sleep state of the sleeper is determined to be the REM sleep state, the presentation control unit 324 refers to a table of the awakening information storage unit 331 illustrated in FIG. 4, and specifies the awakening probability of 0.25 associated with the REM sleep state. Then, the presentation control unit 324 generates presentation screen information indicating "Yamada in bedroom is in REM sleep state. If you enter the room now, probability of awakening Yamada is 25%". Note that the biological information measurement device 1 has information related to the user who measures biological information registered in advance, and can specify who is the sleeper in the bedroom based on the information registered in advance. The display unit 42 of the display device 4 displays the presentation screen information shown in FIG. 7. As shown in FIG. 7, the presentation screen information presents the sleep state of the sleeper in the bedroom and the awakening probability of the sleeper.

Returning to FIG. 5, next, the room entry determination signal receiving unit 312 receives the room entry determination signal transmitted by the room entry detection device 2 (step S6). The communication unit 23 of the room entry detection device 2 transmits, to the server apparatus 3, the room entry determination signal indicating whether or not a person enters the bedroom.

Next, the awakening determination unit 322 determines whether or not a person enters the bedroom based on the room entry determination signal received by the room entry determination signal receiving unit 312 (step S7). In a case where the room entry determination signal indicates that the person enters the bedroom, the awakening determination unit 322 determines that the person enters the bedroom. Further, in a case where the room entry determination signal indicates that no person enters the bedroom, the awakening determination unit 322 determines that no person enters the bedroom.

Here, in a case where it is determined that no person enters the bedroom (NO in step S7), the processing returns to step S1.

On the other hand, in a case where a person is determined to enter the bedroom (YES in step S7), the biological information receiving unit 311 receives the biological information transmitted by the biological information measurement device 1 (step S8).

Next, the sleep state determination unit 321 determines a sleep state of a sleeper based on the biological information of the sleeper received by the biological information receiving unit 311 (step S9).

Next, the awakening determination unit 322 determines whether or not the sleep state of the sleeper changes to the awake state (step S10). The awakening determination unit 322 determines whether or not the sleep state of the sleeper changes from any of the REM sleep state, the light sleep state, and the deep sleep state to the awake state.

Here, in a case where the sleep state of the sleeper is determined not to change to the awake state (NO in step S10), the awakening determination unit 322 determines whether or not a predetermined time has elapsed since the time point of entry at which a person is determined to enter the bedroom (step S11). Note that the predetermined time is, for example, 3 minutes.

Further, in the first embodiment, the awakening determination unit 322 determines whether or not a predetermined time has elapsed since the time point of entry at which the person is determined to enter the bedroom. However, the present disclosure is not particularly limited to this. The room entry determination signal may include a time at which the room entry determination unit 22 of the room entry detection device 2 determines that a person enters the bedroom, and, in this case, the awakening determination unit 322 may determine whether or not a predetermined time has elapsed since the time included in the room entry determination signal. Further, the awakening determination unit 322 may also determine whether or not a predetermined time has elapsed since a time at which the room entry determination signal indicating that a person enters the bedroom is received by the room entry determination signal receiving unit 312 or a time at which the room entry determination signal indicating that a person enters the bedroom is transmitted by the communication unit 23.

In a case where a predetermined time is determined not have elapsed since the time point of entry at which the person is determined to enter the bedroom (NO in step S11), the processing returns to step S8.

On the other hand, in a case where a predetermined time is determined to have elapsed since the time point of entry at which the person is determined to enter the bedroom (YES in step S11), the awakening information generation unit 323 adds 1 to the number of times of entry associated with the sleep state before the time point of entry (step S12).

On the other hand, in a case where the sleep state of the sleeper is determined to change to the awake state (YES in step S10), the awakening information generation unit 323 adds 1 to each of the number of times of entry and the number of times of awakening associated with the sleep state before the time point of entry (step S13).

Next, the awakening information generation unit 323 calculates the awakening probability based on the number of times of entry and the number of times of awakening associated with the sleep state before the time point of entry (step S14).

Next, the awakening information generation unit 323 stores the calculated awakening probability in the awakening information storage unit 331 in association with the sleep state before the time point of entry (step S15).

As described above, the awakening information for determining the possibility of a person awakened by the entry of an object in a case where the person is in the sleep state before the time point of entry at which a person (object) is estimated to enter the bedroom (space) is generated in association with the sleep state before the time point of entry, and the awakening information associated with the sleep state is presented via the display device 4. Accordingly, entry of an object into space where the sleeper is present can be controlled according to the ease of awakening of each sleeper. As a result, the risk of awakening a sleeper even in space where an object may enter can be reduced. Further, an object can be caused to enter the space without awakening the sleeper.

Note that, since the awakening probability can be calculated from the number of times of entry and the number of times of awakening, the awakening information storage unit 331 may be configured to store only the number of times of entry and the number of times of awakening in association with the sleep state. In this case, the processing of steps S14 and S15 of FIG. 6 is not performed, and, in step S3 of FIG. 5, the awakening information generation unit 323 may calculate the awakening probability based on the number of times of entry and the number of times of awakening stored in the awakening information storage unit 331.

Further, in the first embodiment, the presentation control unit 324 presents the probability that the sleeper awakens. However, the present disclosure is not particularly limited to this, and may present the probability that the sleeper does not awaken.

Further, in the first embodiment, the information presentation system may further include a key device that locks and unlocks a door of a bedroom. In a case where the awakening probability of the sleeper is equal to or greater than the threshold, the server apparatus 3 may generate room entry control information for locking the door of the bedroom and transmit the generated room entry control information to the key device. The key device may lock the door based on the received room entry control information. In this manner, in a case where the probability that a sleeper awakens is high, a person who enters the bedroom can be restricted and comfortable sleep can be provided.

Second Embodiment

In the second embodiment, transition of a sleep state of a sleeper after a person enters the bedroom is reflected to the awakening probability.

Figure 8:
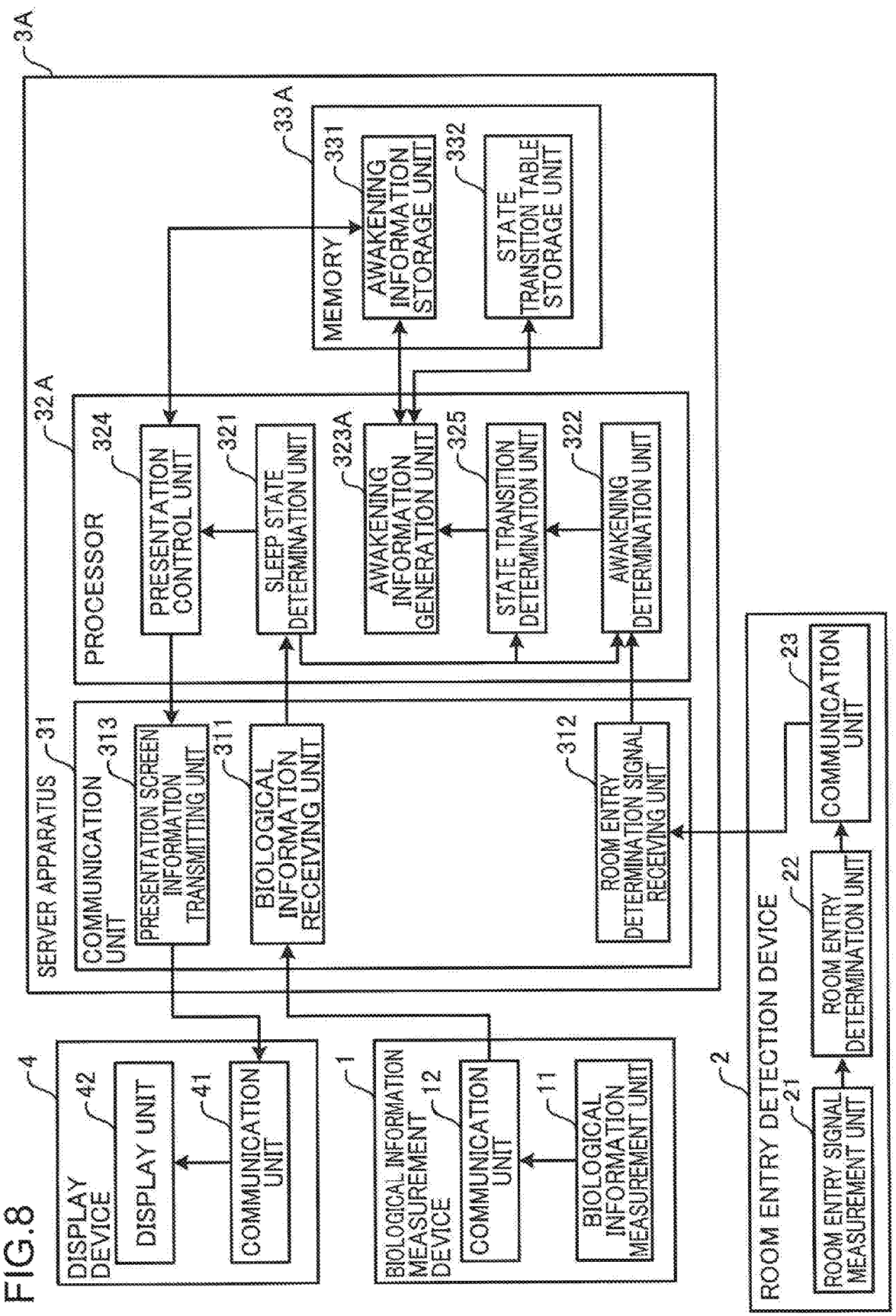
FIG. 8 is a block diagram showing a configuration of the information presentation system in a second embodiment.

FIG. 8 is a block diagram showing a configuration of the information presentation system in the second embodiment. Note that, in the second embodiment, configurations which are the same as those of the first embodiment will be denoted by the same reference numerals and will be omitted from description.

The information presentation system shown in FIG. 8 includes the biological information measurement device 1, the room entry detection device 2, a server apparatus 3A, and the display device 4.

The server apparatus 3A includes the communication unit 31, a processor 32A, and a memory 33A. The processor 32A includes the sleep state determination unit 321, the awakening determination unit 322, an awakening information generation unit 323A, the presentation control unit 324, and a state transition determination unit 325. The memory 33A includes the awakening information storage unit 331 and a state transition table storage unit 332.

The state transition determination unit 325 performs second determination for determining transition of a sleep state after the sleep state changes to awakening based on the sleep state.

The state transition table storage unit 332 stores a state transition table in which transition of the sleep state of the sleeper after a person enters the bedroom and a score (weight value) added to the number of times of awakening are associated with each other.

The awakening information generation unit 323A generates awakening information based on a result of the first determination by the awakening determination unit 322 and a result of the second determination by the state transition determination unit 325. The awakening information generation unit 323A generates awakening information based on whether or not transition is determined to be made in the sleep state from awakening to another state in the second determination. The awakening information generation unit 323A generates awakening information based on elapsed time from a time point at which the sleep state is changed to awakening to a time point at which transition is determined to be made in the sleep state from awakening to another state in the second determination. The awakening information generation unit 323A refers to the state transition table stored in the state transition table storage unit 332, and adds a score corresponding to elapsed time after the sleep state of the sleeper changes to the awake state to the number of times of awakening.

FIG. 9 is a diagram showing an example of the state transition table stored in the state transition table storage unit in the second embodiment.

As shown in FIG. 9, in a case where the sleep state of the sleeper does not change to the awake state within a predetermined time after a person enters the bedroom, the score added to the number of times of awakening is 0. Further, in a case where the sleep state of the sleeper changes to the awake state within a predetermined time after a person enters the bedroom, and transition is made from the awake state to the REM sleep state, the light sleep state, or the deep sleep state within 1 minute, the score added to the number of times of awakening is 0.25. Further, in a case where the sleep state of the sleeper changes to the awake state within a predetermined time after a person enters the bedroom, and transition is made from the awake state to the REM sleep state, the light sleep state, or the deep sleep state within 2 minutes, the score added to the number of times of awakening is 0.5. Further, in a case where the sleep state of the sleeper changes to the awake state within a predetermined time after a person enters the bedroom, and transition is made from the awake state to the REM sleep state, the light sleep state, or the deep sleep state within 3 minutes, the score added to the number of times of awakening is 0.75. Further, in a case where the sleep state of the sleeper changes to the awake state within a predetermined time after a person enters the bedroom, and the awake state continues for 3 minutes or more, or the sleeper leaves the bed within 3 minutes, the score added to the number of times of awakening is 1.0. Note that the score added to the number of times of awakening is an example and is not limited to this.

For example, in a case where a person enters the bedroom when the sleep state of the sleeper is the light sleep state, the sleep state of the sleeper changes to the awake state within a predetermined time after the person enters the bedroom, and transition is made from the awake state to the REM sleep state, the light sleep state, or the deep sleep state within 2 minutes, 0.5 is added to the number of times of awakening and 1 is added to the number of times of entry.

FIG. 10 is a first flowchart for describing operation of the server apparatus according to the second embodiment of the present disclosure. FIG. 11 is a second flowchart for describing the operation of the server apparatus according to the second embodiment of the present disclosure.

Note that the processing in steps S21 to S32 shown in FIGS. 10 and 11 is the same as the processing in steps S1 to S12 shown in FIGS. 5 and 6, and will be omitted from description.

Next, in a case where the sleep state of the sleeper is determined to change to the awake state (YES in step S30), the biological information receiving unit 311 receives the biological information transmitted by the biological information measurement device 1 (step S33).

Next, the sleep state determination unit 321 determines the sleep state of the sleeper based on the biological information of the sleeper received by the biological information receiving unit 311 (step S34).

Next, the state transition determination unit 325 determines whether or not transition is made in the sleep state of the sleeper from the awake state to the REM sleep state, the light sleep state, or the deep sleep state (step S35). The state transition determination unit 325 determines whether or not the sleep state of the sleeper changes from the awake state to another sleep state.

Here, in a case where transition is determined not to be made in the sleep state of the sleeper from the awake state to the REM sleep state, the light sleep state, or the deep sleep state (NO in step S35), the awakening information generation unit 323A determines whether or not 3 minutes or more have elapsed since a time point at which the sleep state changes to the awake state (step S36). Note that 3 minutes, which is a determination standard for the elapsed time, is an example, and the present disclosure is not particularly limited to this.

In a case where 3 minutes or more are determined not to have elapsed since the time point at which the sleep state of the sleeper changes to the awake state (NO in step S36), the processing returns to step S33.

On the other hand, in a case where 3 minutes or more are determined to have elapsed since the time point at which the sleep state of the sleeper changes to the awake state (YES in step S36), the awakening information generation unit 323A adds 1 to each of the number of times of entry and the number of times of awakening associated with the sleep state before the time point of entry in step S37 (step S37).

On the other hand, in a case where transition is determined to be made in the sleep state of the sleeper from the awake state to the REM sleep state, the light sleep state, or the deep sleep state (YES in step S35), the awakening information generation unit 323A adds 1 to the number of times of entry associated with the sleep state before the time point of entry, and refers to the state transition table stored in the state transition table storage unit 332 to add, to the number of times of awakening, a score corresponding to the elapsed time since the time point at which the sleep state of the sleeper changes to the awake state (step S38). For example, if the elapsed time since the time point at which the sleep state of the sleeper changes to the awakening state is within 1 minute, the awakening information generation unit 323A adds 0.25 to the number of times of awakening. Further, if the elapsed time since the time point at which the sleep state of the sleeper changes to the awakening state is within 2 minutes, the awakening information generation unit 323A adds 0.5 to the number of times of awakening. Further, if the elapsed time since the time point at which the sleep state of the sleeper changes to the awakening state is within 3 minutes, the awakening information generation unit 323A adds 0.75 to the number of times of awakening.

Note that the processing in steps S39 and S40 shown in FIG. 11 is the same as the processing in steps S14 and S15 shown in FIG. 6, and will be omitted from description.

As described above, since transition of the sleep state after the sleep state of the sleeper changes to the awake state due to a person entering the bedroom is reflected in the awakening probability, the accuracy of the awakening probability can be improved.

Note that, since the awakening probability can be calculated from the number of times of entry and the number of times of awakening, the awakening information storage unit 331 may be configured to store only the number of times of entry and the number of times of awakening in association with the sleep state. In this case, the processing of steps S39 and S40 of FIG. 11 is not performed, and, in step S23 of FIG. 10, the awakening information generation unit 323A may calculate the awakening probability based on the number of times of entry and the number of times of awakening stored in the awakening information storage unit 331.

Further, the biological information receiving unit 311 may determine whether or not biological information exists before receiving the biological information in step S33 of FIG. 11. In a case where the sleeper leaves the bed, biological information is no longer detected. For this reason, whether or not the sleeper leaves the bed can be determined by determining whether or not biological information exists. Then, in a case where the biological information is determined not to exist, the processing proceeds to step S37. In a case where the biological information is determined to exist, the processing proceeds to step S33.

Third Embodiment

In the third embodiment, presentation of the awakening information in a case where a plurality of sleepers are sleeping in the bedroom will be described.

Figure 12:
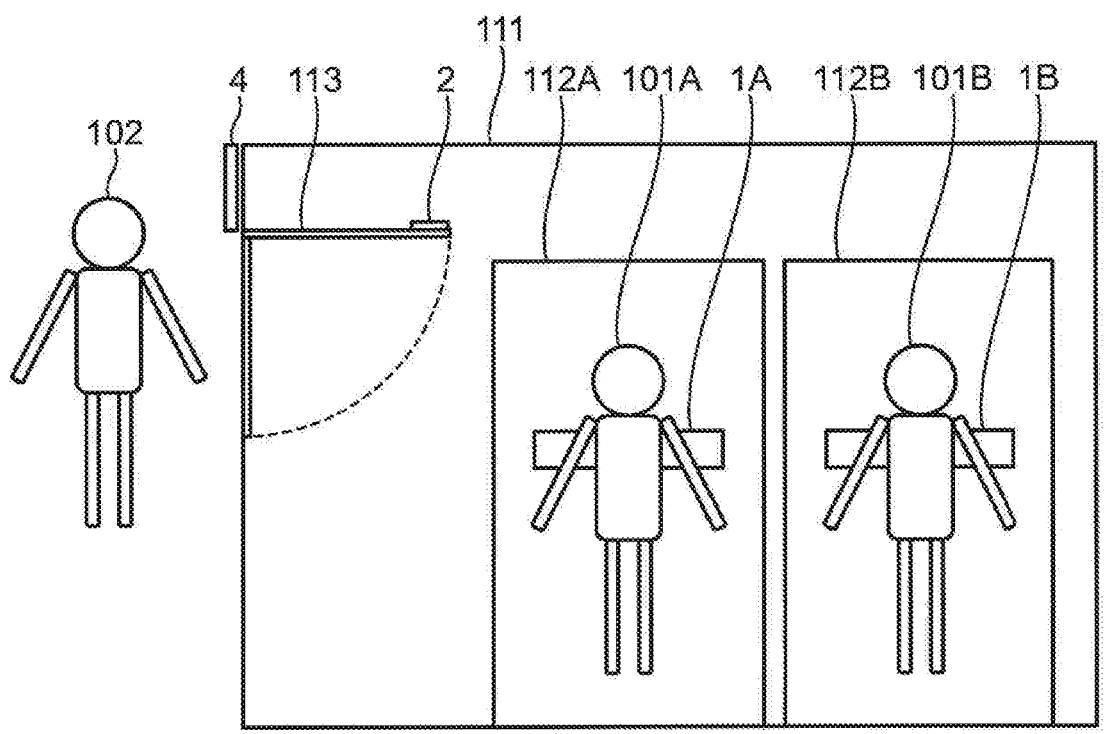
FIG. 12 is a diagram showing an example of a bedroom in which a plurality of the biological information measurement devices, the room entry detection device, and the display device are disposed in a third embodiment.

FIG. 12 is a diagram showing an example of a bedroom in which a plurality of the biological information measurement devices, the room entry detection device, and the display device are disposed in the third embodiment. Note that, in the third embodiment, configurations which are the same as those of the first embodiment will be denoted by the same reference numerals and will be omitted from description.

As shown in FIG. 12, a bed mattress 112A on which a first sleeper 101A sleeps and a bed mattress 112B on which a second sleeper 101B sleeps are disposed in the bedroom 111.

A first biological information measurement device 1A is installed, for example, under the bed mattress 112A, and measures biological information, such as a heart rate, a respiratory rate, and a body movement amount, of the first sleeper 101A.

A second biological information measurement device 1B is installed, for example, under the bed mattress 112B, and measures biological information, such as a heart rate, a respiratory rate, and a body movement amount, of the second sleeper 101B.

Note that, in the third embodiment, two sleepers are sleeping in the bedroom 111. However, the present disclosure is not particularly limited to this, and three or more sleepers may be sleeping, and, in this case, the biological information measurement device that measures the biological information of each sleeper is disposed.

Figure 13:
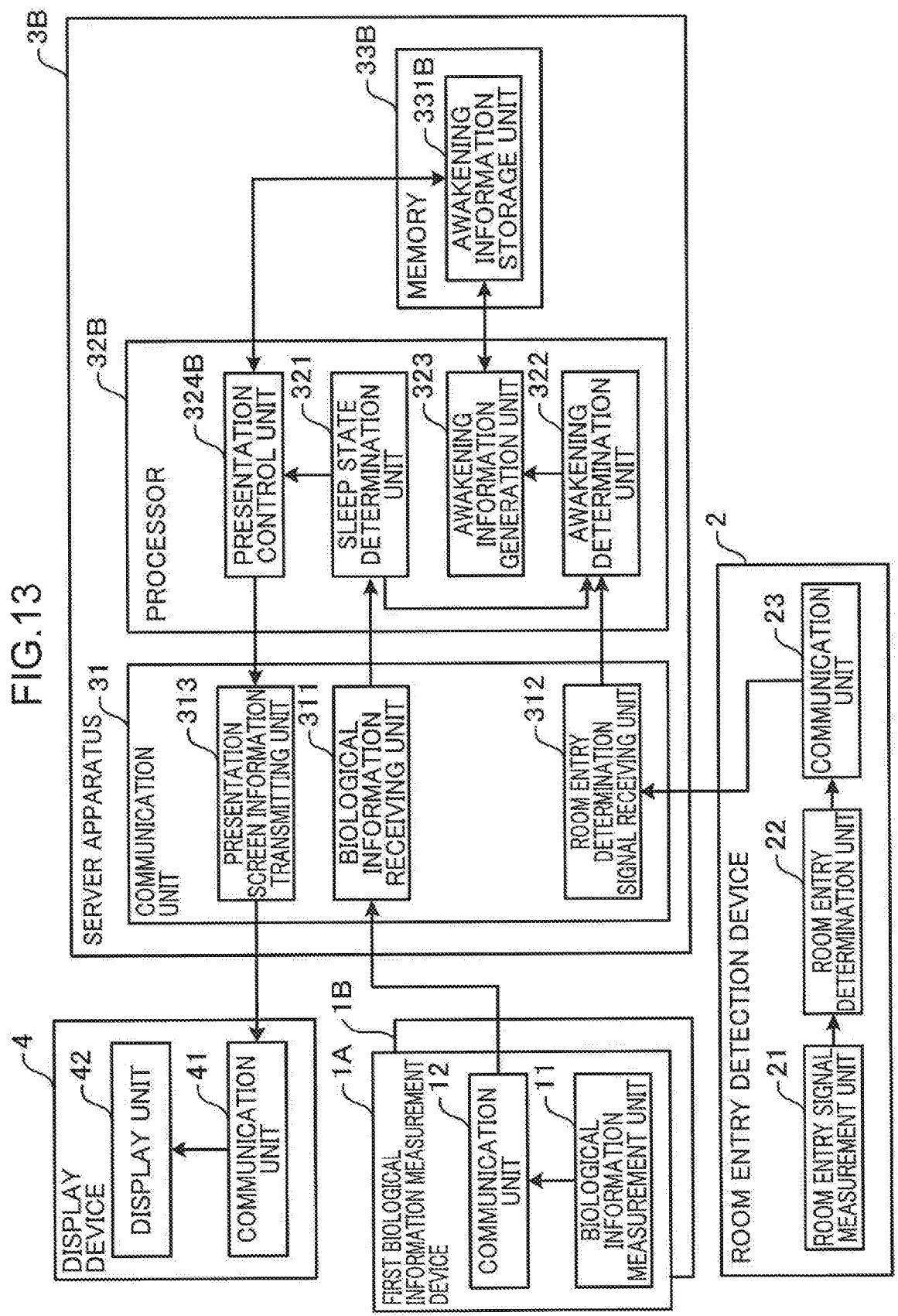
FIG. 13 is a block diagram showing a configuration of the information presentation system in the third embodiment.

FIG. 13 is a block diagram showing a configuration of the information presentation system in the third embodiment.

The information presentation system shown in FIG. 13 includes the first biological information measurement device 1A, the second biological information measurement device 1B, the room entry detection device 2, a server apparatus 3B, and the display device 4.

The configurations of the first biological information measurement device 1A and the second biological information measurement device 1B are the same as the configuration of the biological information measurement device 1 in the first embodiment.

The server apparatus 3B includes the communication unit 31, a processor 32B, and a memory 33B. The processor 32B includes the sleep state determination unit 321, the awakening determination unit 322, the awakening information generation unit 323, a presentation control unit 324B, and a state transition determination unit 325. The memory 33B includes an awakening information storage unit 331B.

The biological information receiving unit 311 receives the biological information transmitted by the first biological information measurement device 1A, and also receives the biological information transmitted by the second biological information measurement device 1B. The biological information receiving unit 311 outputs the received biological information to the sleep state determination unit 321.

The sleep state determination unit 321 determines the sleep state of the first sleeper 101A based on the biological information of the first sleeper 101A received by the biological information receiving unit 311, and also determines the sleep state of the second sleeper 101B based on the biological information of the second sleeper 101B received by the biological information receiving unit 311. The sleep state determination unit 321 acquires the sleep states of a plurality of persons existing in the bedroom 111 (space).

The awakening determination unit 322 performs first determination to determine whether or not the sleep states of the first sleeper 101A and the second sleeper 101B are changed to awakening within a predetermined time from a time point of entry, at which a person (object) is estimated to enter the bedroom 111 (space), based on the sleep states and the room entry determination signal (detection data).

Based on a result of the first determination by the awakening determination unit 322, the awakening information generation unit 323 generates, in association with the sleep state before the time point of entry, awakening information for determining the possibility of a person awakened by the entry of a person (object) in a case where the person is in the sleep state before the time point of entry. The awakening information generation unit 323 generates awakening information for each of the plurality of sleepers.

The awakening information storage unit 331B stores a combination of the number of times of entry and the number of times of awakening and the awakening probability in association with the sleep state before the time point of entry for each of the plurality of sleepers.

FIG. 14 is a diagram showing an example of awakening information stored in the awakening information storage unit in the third embodiment.

As shown in FIG. 14, the awakening information storage unit 331B stores the number of times of entry, the number of times of awakening, and the awakening probability in association with the sleep state for each of the sleepers. The awakening probability associated with the REM sleep state of the first sleeper 101A is 0.25 (25%), the awakening probability associated with the light sleep state of the first sleeper 101A is 0.5 (50%), and the awakening probability associated with the deep sleep state of the first sleeper 101A is 0.04 (4%). Further, the awakening probability associated with the REM sleep state of the second sleeper 101B is 0.3 (30%), the awakening probability associated with the light sleep state of the second sleeper 101B is 0.8 (80%), and the awakening probability associated with the deep sleep state of the second sleeper 101B is 0.08 (8%).

The presentation control unit 324B presents the awakening information associated with the sleep states of the plurality of sleepers via the display device 4 (presentation device). The presentation control unit 324B refers to the awakening information storage unit 331B, specifies awakening information of a sleeper who has the highest possibility of awakening among pieces of the awakening information associated with the sleep states of the plurality of sleepers determined by the sleep state determination unit 321, and generates presentation screen information for presenting the specified awakening information. The presentation screen information is information for presenting the sleep states of the plurality of sleepers and the highest awakening probability among the plurality of awakening probabilities corresponding to the sleep states of the plurality of sleepers.

For example, in FIG. 14, in a case where the first sleeper 101A is in the deep sleep state, the awakening probability of the first sleeper 101A is 4%. Further, in a case where the second sleeper 101B is in the light sleep state, the awakening probability of the second sleeper 101B is 80%. In these cases, the presentation control unit 324B generates presentation screen information for presenting the awakening probability of the second sleeper 101B having the highest awakening probability. The presentation control unit 324B generates presentation screen information indicating, for example, "Yamada in bedroom is in deep sleep state. Suzuki in bedroom is in light sleep state. If you enter the room now, probability of awakening Suzuki is 80%".

As described above, in a case where there are a plurality of sleepers in the bedroom, the highest awakening probability of the plurality of sleepers is presented. Accordingly, by preventing a person from entering the bedroom, comfortable sleep of all the sleepers can be realized.

Fourth Embodiment

In a fourth embodiment, in a case where the awakening probability is higher than a threshold, information that suppresses entry into the bedroom is presented, and, in a case where the awakening probability is equal to or less than the threshold, information that permits entry into the bedroom is presented.

Figure 15:
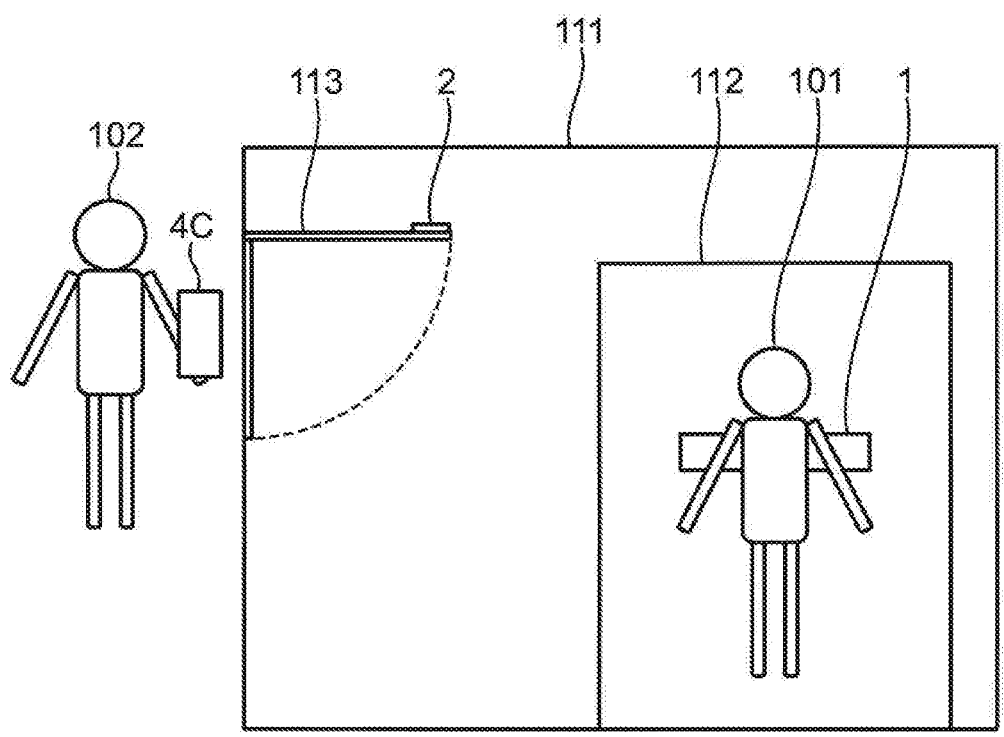
FIG. 15 is a diagram showing an example of a bedroom in which the biological information measurement device, the room entry detection device, and the display device are disposed in a fourth embodiment.

FIG. 15 is a diagram showing an example of a bedroom in which the biological information measurement device, the room entry detection device, and the display device are disposed in the fourth embodiment. Note that, in the fourth embodiment, configurations which are the same as those of the first embodiment will be denoted by the same reference numerals and will be omitted from description.

As shown in FIG. 15, a display device 4C in the fourth embodiment is, for example, a terminal device, such as a smartphone or a tablet computer, and is carried by the entering person 102. For this reason, the entering person 102 can check the awakening information of the sleeper 101 in the bedroom by using the display device 4C that the entering person 102 carries without going to the front of the bedroom 111.

Figure 16:
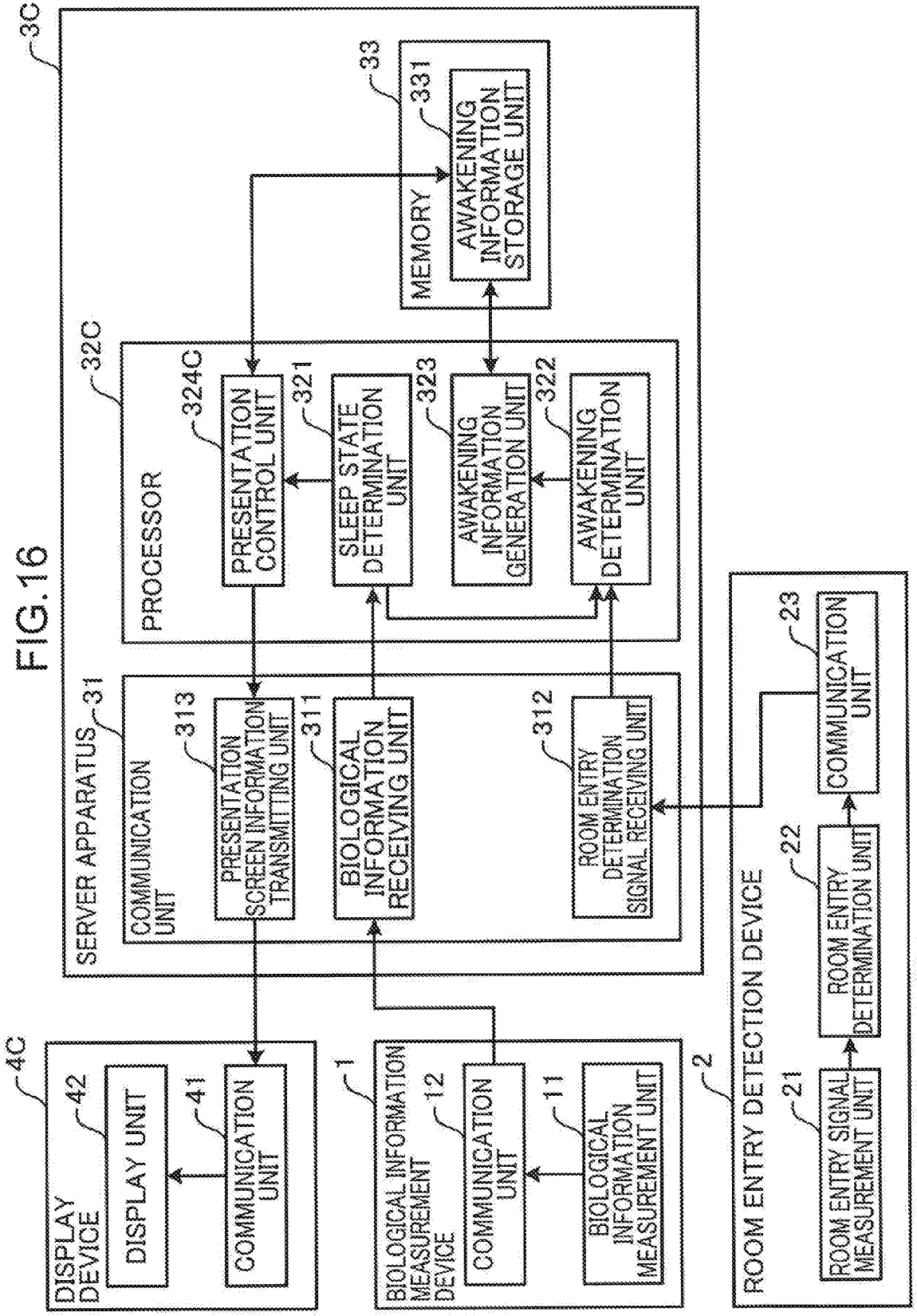
FIG. 16 is a block diagram showing a configuration of the information presentation system in the fourth embodiment.

FIG. 16 is a block diagram showing a configuration of the information presentation system in the fourth embodiment.

The information presentation system shown in FIG. 16 includes the biological information measurement device 1, the room entry detection device 2, a server apparatus 3C, and the display device 4C.

The server apparatus 3C includes the communication unit 31, a processor 32C, and the memory 33. The processor 32C includes the sleep state determination unit 321, the awakening determination unit 322, the awakening information generation unit 323, and a presentation control unit 324C.

The presentation control unit 324C refers to the awakening information storage unit 331 to specify the awakening probability associated with the sleep state determined by the sleep state determination unit 321. The presentation control unit 324C determines whether or not the specified awakening probability is higher than a threshold. Note that the threshold is, for example, 0.05 (5%). In a case where the specified awakening probability is higher than the threshold, the presentation control unit 324C generates room entry suppression screen information for suppressing entry into the bedroom. Further, in a case where the specified awakening probability is equal to or less than the threshold, the presentation control unit 324C generates room entry permission screen information for permitting entry into the bedroom.

The configuration of the display device 4C is the same as the configuration of the display device 4 of the first embodiment.

Figure 17:
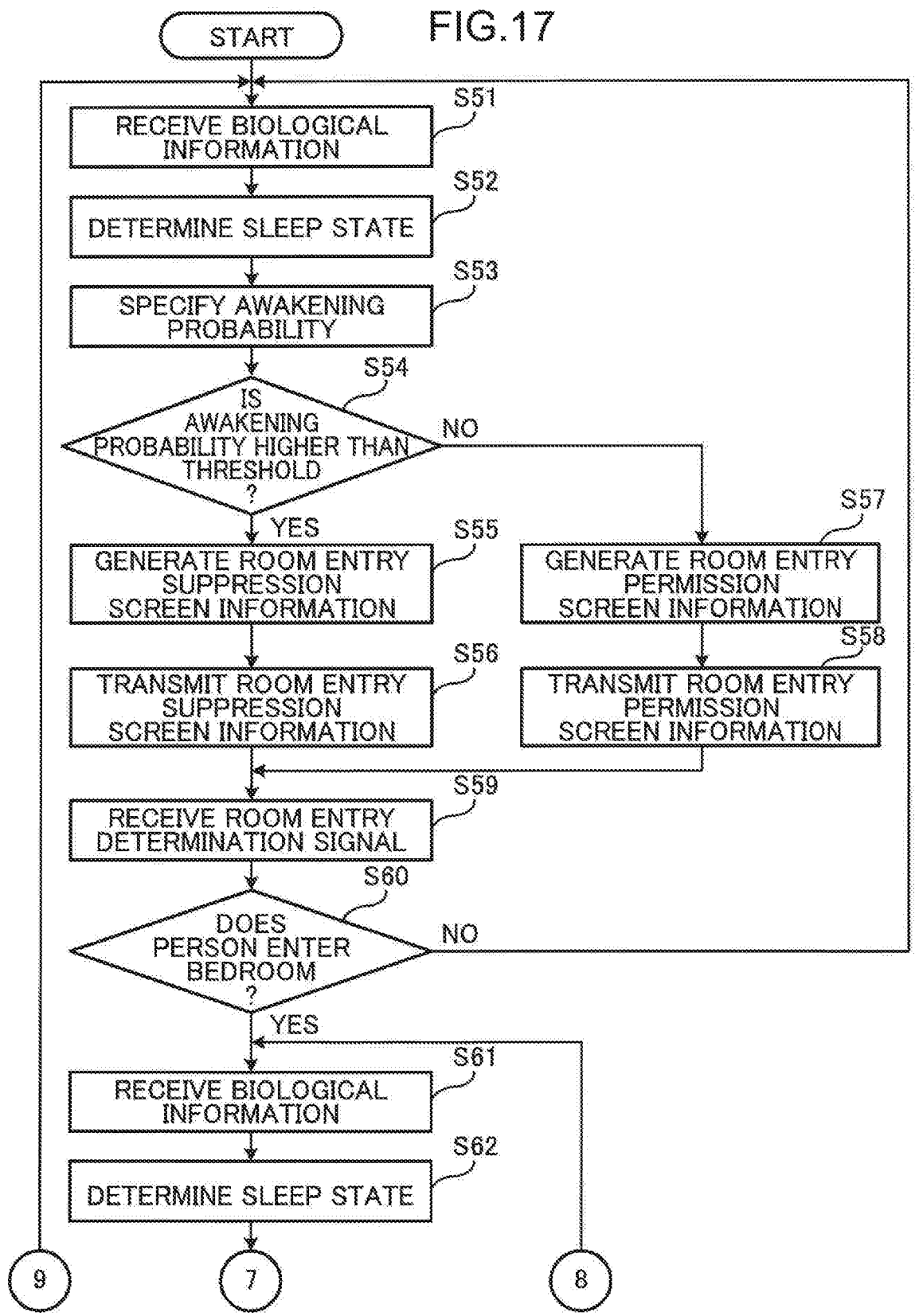
FIG. 17 is a first flowchart for describing operation of the server apparatus in the fourth embodiment of the present disclosure.
Figure 18:
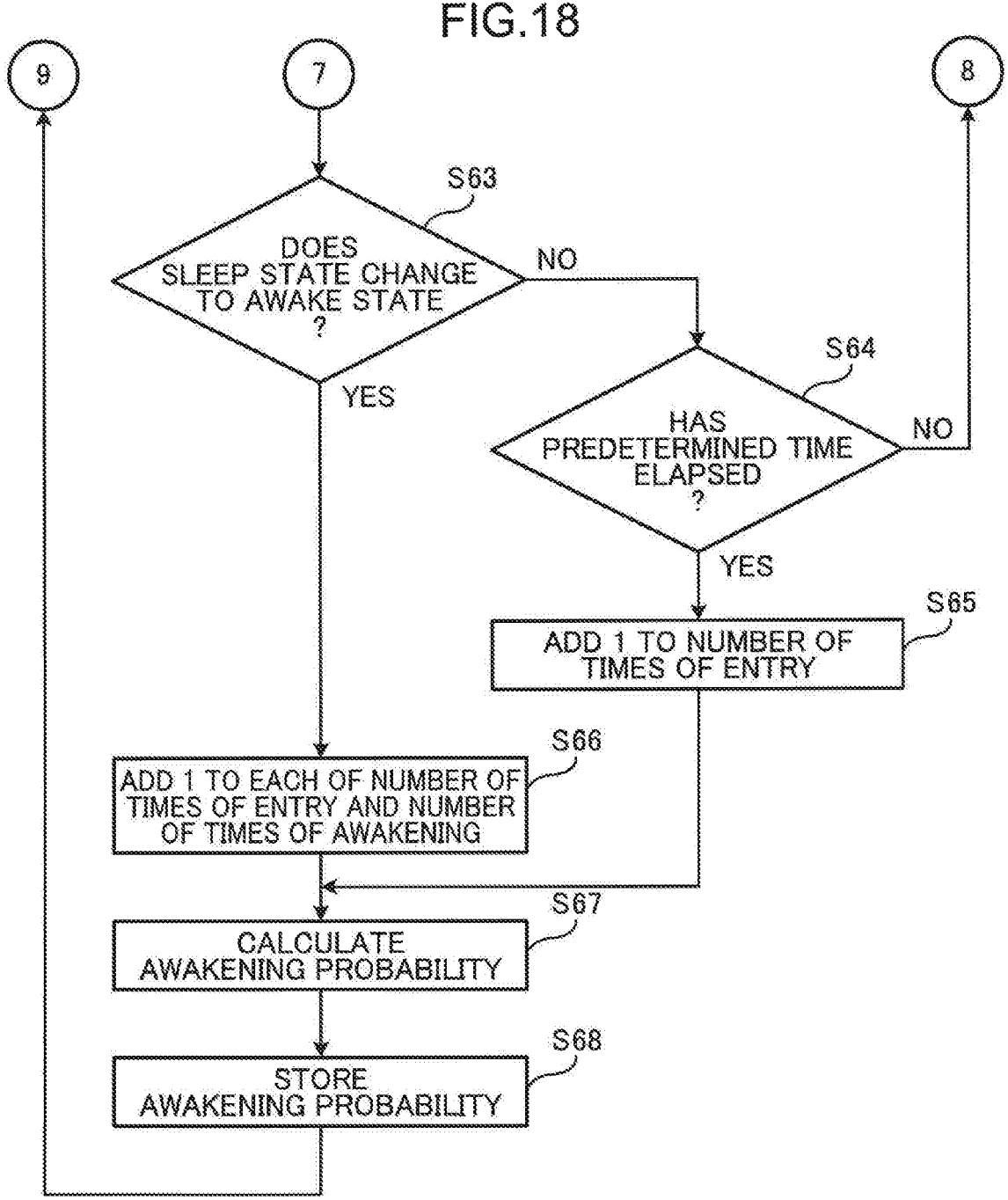
FIG. 18 is a second flowchart for describing operation of the server apparatus in the fourth embodiment of the present disclosure.

FIG. 17 is a first flowchart for describing operation of the server apparatus according to the fourth embodiment of the present disclosure. FIG. 18 is a second flowchart for describing the operation of the server apparatus according to the fourth embodiment of the present disclosure.

Note that the processing in steps S41 to S43 shown in FIG. 17 is the same as the processing in steps S1 to S3 shown in FIG. 5, and will be omitted from description.

Next, the presentation control unit 324C determines whether or not the specified awakening probability is higher than the threshold (step S54). Here, in a case where the specified awakening probability is determined to be higher than the threshold (YES in step S54), the presentation control unit 324C presents the specified awakening probability and generates the room entry suppression screen information for suppressing entry into the bedroom (step S55).

Next, the presentation screen information transmitting unit 313 transmits the room entry suppression screen information generated by the presentation control unit 324C to the display device 4C (step S56). The communication unit 41 of the display device 4C receives the room entry suppression screen information transmitted by the server apparatus 3C. The display unit 42 displays the room entry suppression screen information received by the communication unit 41.

FIG. 19 is a diagram showing an example of the room entry suppression screen information displayed on the display device in the fourth embodiment.

In a case where the sleep state of the sleeper is determined to be the light sleep state, the presentation control unit 324C refers to a table of the awakening information storage unit 331 illustrated in FIG. 4, and specifies the awakening probability of 0.5 associated with the light sleep state. Then, the presentation control unit 324C generates the room entry suppression screen information indicating "Yamada in bedroom is in light sleep state. If you enter the room now, probability of awakening Yamada is 50%. Please do not enter the room". The display unit 42 of the display device 4C displays the room entry suppression screen information shown in FIG. 19. As shown in FIG. 19, the room entry suppression screen information presents the sleep state of the sleeper in the bedroom, the awakening probability of the sleeper, and the message that suppresses the entry into the bedroom.

Returning to FIG. 17, in a case where the specified awakening probability is determined to equal to or less than the threshold (NO in step S54), the presentation control unit 324C presents the specified awakening probability and generates the room entry permission screen information for permitting entry into the bedroom (step S57).

Next, the presentation screen information transmitting unit 313 transmits the room entry permission screen information generated by the presentation control unit 324C to the display device 4C (step S58). The communication unit 41 of the display device 4C receives the room entry permission screen information transmitted by the server apparatus 3C. The display unit 42 displays the room entry permission screen information received by the communication unit 41.

FIG. 20 is a diagram showing an example of the room entry permission screen information displayed on the display device in the fourth embodiment.

In a case where the sleep state of the sleeper is determined to be the deep sleep state, the presentation control unit 324C refers to a table of the awakening information storage unit 331 illustrated in FIG. 4, and specifies the awakening probability of 0.04 associated with the deep sleep state. Then, the presentation control unit 324C generates the room entry permission screen information indicating "Yamada in bedroom is in deep sleep state. If you enter the room now, probability of awakening Yamada is 4%. Please open and close door as quietly as possible to enter the room". The display unit 42 of the display device 4C displays the room entry permission screen information shown in FIG. 20. As shown in FIG. 20, the room entry permission screen information presents the sleep state of the sleeper in the bedroom, the awakening probability of the sleeper, and the message that permits the entry into the bedroom.

Note that the processing in steps S59 to S68 shown in FIGS. 17 and 18 is the same as the processing in steps S6 to S15 shown in FIGS. 5 and 6, and will be omitted from description.

As described above, in a case where the awakening probability of the sleeper becomes equal to or less than the threshold and the sleeper is in a state of being unlikely to awaken, the room entry permission screen information that permits entry into the bedroom is notified to an entering person. Accordingly, a time period in which the entering person is caused to wait in front of the bedroom can be shortened. Further, since a person enters the bedroom when the sleeper is unlikely to awaken, more comfortable sleep can be provided to the sleeper.

Fifth Embodiment

The awakening of the sleeper caused by a person entering the bedroom is related to the sleep state of the sleeper and the environment, such as sound or light, which changes when the person enters the bedroom. In view of the above, in a fifth embodiment, sound data in the bedroom when a person enters the bedroom is acquired, and a characteristic of the acquired sound data is associated with the awakening information.

Figure 21:
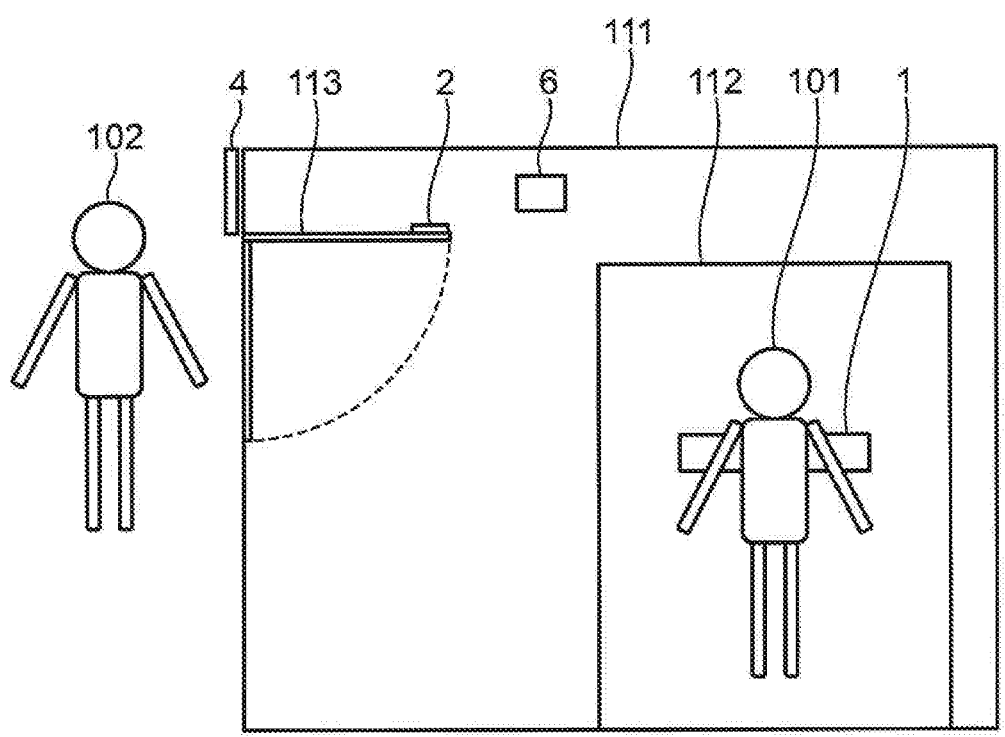
FIG. 21 is a diagram showing an example of a bedroom in which the biological information measurement device, the room entry detection device, the display device, and a sound acquisition device are disposed in a fifth embodiment.

FIG. 21 is a diagram showing an example of a bedroom in which the biological information measurement device, the room entry detection device, the display device, and a sound acquisition device are disposed in the fifth embodiment. Note that, in the fifth embodiment, configurations which are the same as those of the first embodiment will be denoted by the same reference numerals and will be omitted from description.

A sound acquisition device 6 is disposed in the bedroom 111, acquires a sound in the bedroom 111, and transmits the acquired sound data to the server apparatus.

Figure 22:
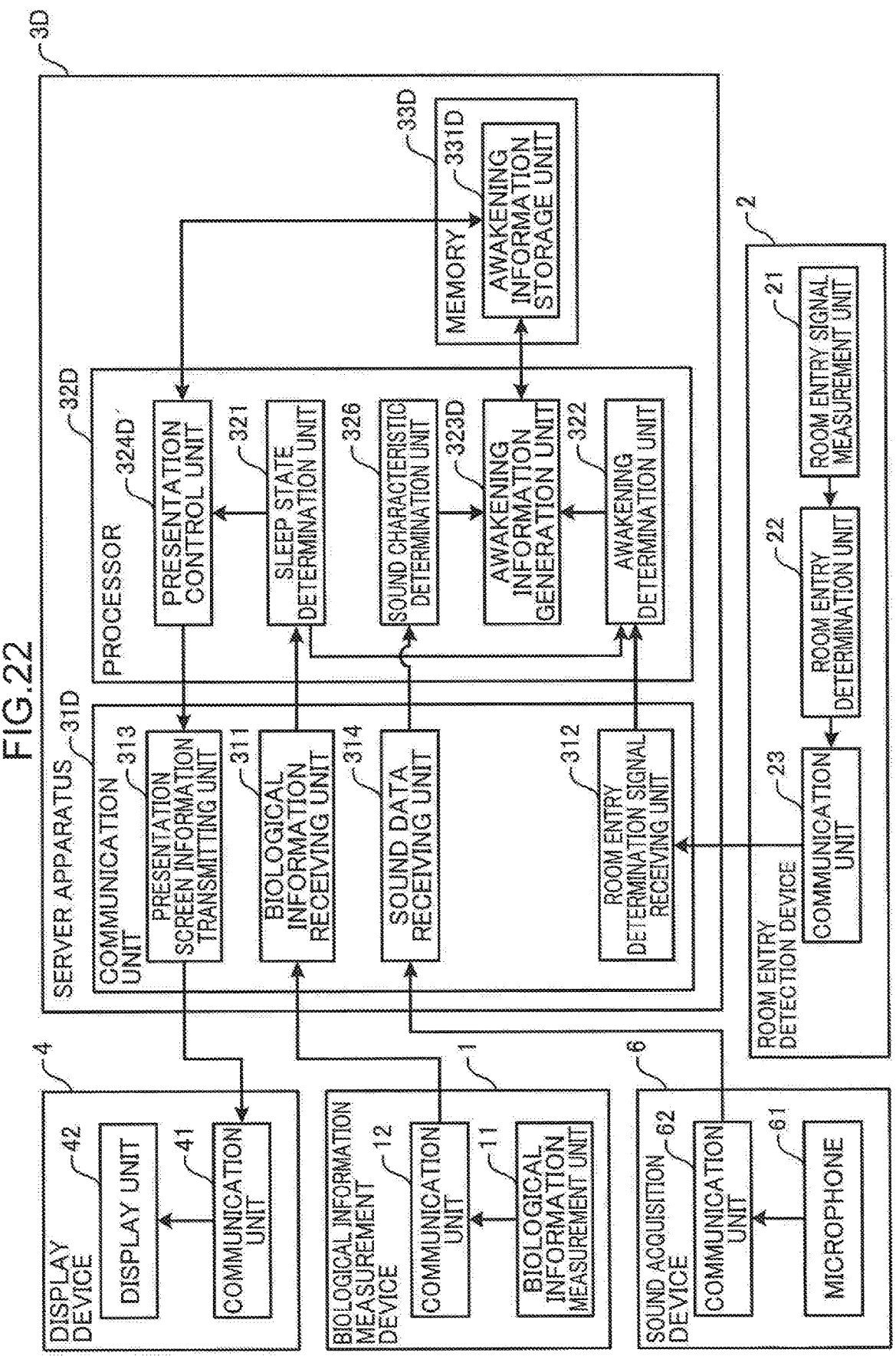
FIG. 22 is a block diagram showing a configuration of the information presentation system in the fifth embodiment.

FIG. 22 is a block diagram showing a configuration of the information presentation system in the fifth embodiment.

The information presentation system shown in FIG. 22 includes the biological information measurement device 1, the room entry detection device 2, a server apparatus 3D, the display device 4, and the sound acquisition device 6.

The sound acquisition device 6 includes a microphone 61 and a communication unit 62. The microphone 61 acquires sound data in the bedroom. The microphone 61 periodically acquires sound data at a predetermined time interval. The communication unit 62 transmits the sound data acquired by the microphone 61 to the server apparatus 3D. The communication unit 62 periodically transmits sound data at a predetermined time interval.

The server apparatus 3D includes a communication unit 31D, a processor 32D, and a memory 33D. The communication unit 31D includes the biological information receiving unit 311, the room entry determination signal receiving unit 312, the presentation screen information transmitting unit 313, and a sound data receiving unit 314. The processor 32D includes the sleep state determination unit 321, the awakening determination unit 322, an awakening information generation unit 323D, a presentation control unit 324D, and a sound characteristic determination unit 326. The memory 33D includes an awakening information storage unit 331D.

The sound data receiving unit 314 receives sound data transmitted by the sound acquisition device 6. The sound data receiving unit 314 acquires sound data output from the microphone 61 present in the bedroom (space).

The sound characteristic determination unit 326 uses the sound data and the room entry determination signal (detection data) to determine a characteristic of a sound in the bedroom (space) within a predetermined time from a time point at which a person (object) is estimated to enter the bedroom (space). Note that the characteristic of the sound is, for example, a sound volume. Further, the characteristic of the sound may be, for example, a sound pressure, a frequency, or reverberation.

The awakening information generation unit 323D associates the characteristic of the sound determined by the sound characteristic determination unit 326 with the awakening information. Based on a result of the first determination by the awakening determination unit 322 and a determination result of the characteristic of the sound by the sound characteristic determination unit 326, the awakening information generation unit 323D generates, for each sound volume (the characteristic of the sound), awakening information for determining the possibility of a person being awakened by the entry of a person (object) in a case where the person is in the sleep state before the time point of entry. The awakening information generation unit 323D further associates the awakening information for each sound volume (the characteristic of the sound) with the sleep state before the time point of entry.

The awakening information generation unit 323, for example, counts, for each sound volume, a combination of the number of times of entry indicating the number of times another person enters a room while a sleeper is sleeping, and the number of times of awakening indicating the number of times a sleep state of the sleeper changes to awakening within a predetermined time from the time point of entry at which the other person enters the bedroom 111, and generates the awakening probability by dividing the number of times of awakening by the number of times of entry in association with the sleep state before the time point of entry for each sound volume.

The awakening information storage unit 331D stores the number of times of entry, the number of times of awakening, and the awakening probability in association with the sleep state for each sound volume (characteristic of a sound).

The presentation control unit 324D presents the awakening information and the characteristic of the sound associated with the awakening information. The presentation control unit 324D presents the awakening information corresponding to the characteristic of the sound.

Figure 23:
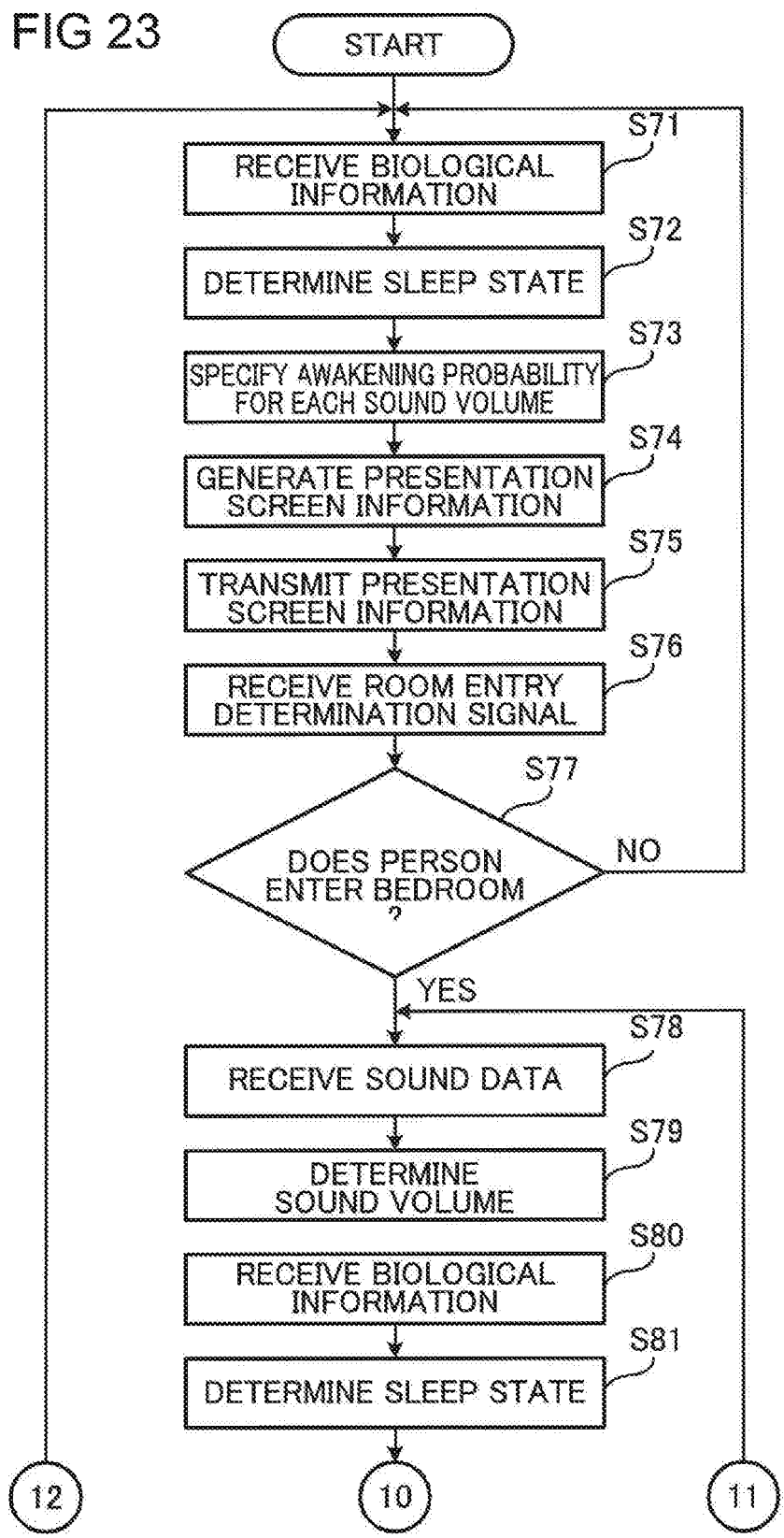
FIG. 23 is a first flowchart for describing operation of the server apparatus in the fifth embodiment of the present disclosure.
Figure 24:
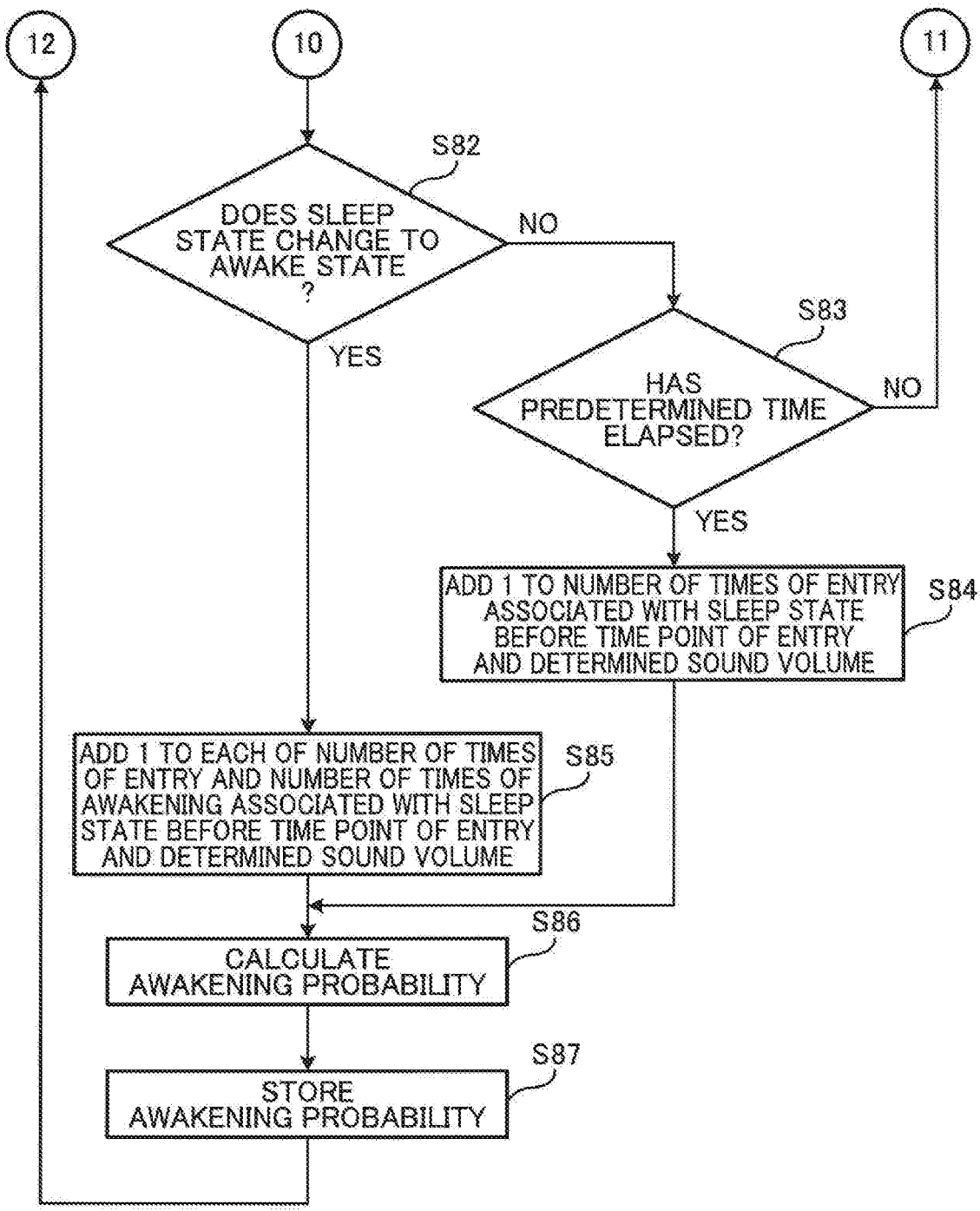
FIG. 24 is a second flowchart for describing operation of the server apparatus in the fifth embodiment of the present disclosure.

FIG. 23 is a first flowchart for describing operation of the server apparatus according to the fifth embodiment of the present disclosure. FIG. 24 is a second flowchart for describing the operation of the server apparatus according to the fifth embodiment of the present disclosure.

Note that the processing in steps S71 and S72 shown in FIG. 23 is the same as the processing in steps S1 and S2 shown in FIG. 5, and will be omitted from description.

Next, the presentation control unit 324D refers to the awakening information storage unit 331D to specify, for each sound volume, the awakening probability associated with the sleep state determined by the sleep state determination unit 321 (step S73). The awakening information storage unit 331D stores the sound volume, the number of times of entry, the number of times of awakening, and the awakening probability in association with each other for each sleep state.

For example, for the REM sleep state, the awakening information storage unit 331D stores the sound volume of 10 dB, the number of times of entry of 18, the number of times of awakening of 0, and the awakening probability of 0 associated with each other, the sound volume of 20 dB, the number of times of entry of 13, the number of times of awakening of 0, and awakening probability of 0 associated with each other, the sound volume of 30 dB, the number of times of entry of 9, the number of times of awakening of 1, and the awakening probability of 0.11 associated with each other, the sound volume of 40 dB, the number of times of entry of 6, the number of times of awakening of 2, and the awakening probability of 0.33 associated with each other, the sound volume of 50 dB, the number of times of entry of 7, the number of times of awakening of 5, and the awakening probability of 0.71 associated with each other, and the sound volume of 60 dB, the number of times of entry of 12, the number of times of awakening of 11, and the awakening probability of 0.91 associated with each other.

Note that, in the fifth embodiment, the awakening information storage unit 331D stores the number of times of entry, the number of times of awakening, and the awakening probability in units of 10 dB. However, the present disclosure is not particularly limited to this, and, for example, the number of times of entry, the number of times of awakening, and the awakening probability may be stored in association with each other in units of 1 dB or 5 dB.

Next, the presentation control unit 324D generates presentation screen information for presenting the specified awakening probability (step S74).

Next, the presentation screen information transmitting unit 313 transmits the presentation screen information generated by the presentation control unit 324D to the display device 4 (step S75). The communication unit 41 of the display device 4 receives the presentation screen information transmitted by the server apparatus 3D. The display unit 42 displays the presentation screen information received by the communication unit 41.

Figures 25, 26:
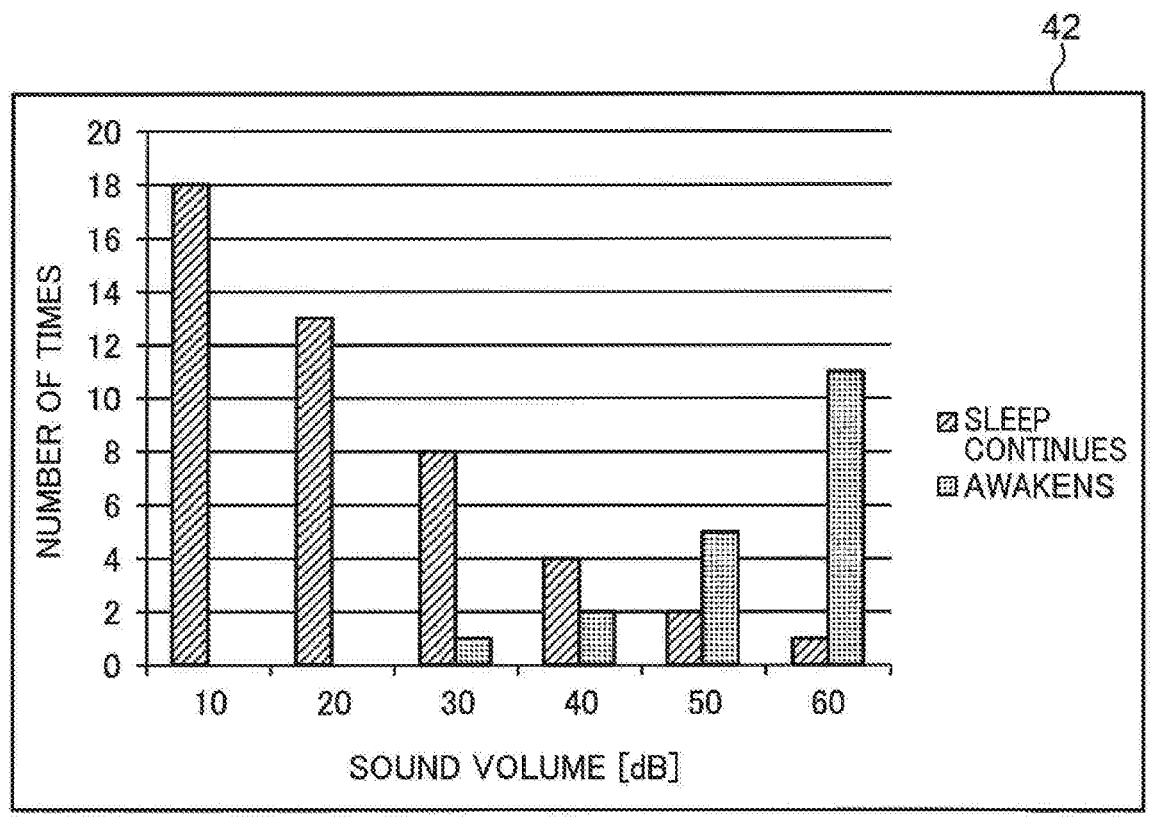
FIG. 25 is a diagram showing an example of presentation screen information displayed on the display device in the fifth embodiment.
FIG. 26 is a diagram showing a first variation of presentation screen information displayed on the display device in the fifth embodiment.

FIG. 25 is a diagram showing an example of the presentation screen information displayed on the display device in the fifth embodiment.

In a case where the sleep state of the sleeper is determined to be the REM sleep state, the presentation control unit 324D refers to a table of the awakening information storage unit 331D, and specifies the awakening probability for each sound volume associated with the REM sleep state. Then, the presentation control unit 324D generates presentation screen information indicating "Yamada in bedroom is in REM sleep state. If you enter the room now, Yamada will not be awakened by sound of 10 to 20 dB. Probability of awakening Yamada is 11% with sound of 30 dB. Probability of awakening Yamada is 33% with sound of 40 dB. Probability of awakening Yamada is 71% with sound of 50 dB. Probability of awakening Yamada is 91% with sound of 60 dB". The display unit 42 of the display device 4 displays the presentation screen information shown in FIG. 25. As shown in FIG. 25, the presentation screen information presents the sleep state of the sleeper in the bedroom and the awakening probability of the sleeper for each sound volume.

As described above, since the awakening probability of the sleeper for each sound volume is presented, an entering person can recognize to what level the sound can be made when entering the bedroom.

The processing in steps S76 and S77 shown in FIG. 23 is the same as the processing in steps S6 and S7 shown in FIG. 5, and will be omitted from description.

Next, in a case where a person is determined to enter the bedroom (YES in step S77), the sound data receiving unit 314 receives the sound data transmitted by the sound acquisition device 6 (step S78).

Next, the sound characteristic determination unit 326 determines a sound volume in the bedroom within a predetermined time from the time point of entry at which a person is determined to enter the bedroom (step S79).

Note that the processing in steps S80 to S83 shown in FIGS. 23 and 24 is the same as the processing in steps S8 to S11 shown in FIGS. 5 and 6, and will be omitted from description.

In a case where a predetermined time is determined to have elapsed since the time point of entry at which the person is determined to enter the bedroom (YES in step S83), the awakening information generation unit 323D adds 1 to the number of times of entry associated with the sleep state before the time point of entry and the sound volume determined by the sound characteristic determination unit 326 (step S84).

Note that, in the fifth embodiment, the awakening information storage unit 331D stores the number of times of entry, the number of times of awakening, and the awakening probability in association with each other in units of 10 dB. For this reason, the awakening information generation unit 323D rounds off the sound volume determined by the sound characteristic determination unit 326, and adds 1 to the number of times of entry associated with the rounded sound volume and the sleep state before the time point of entry. For example, if the sound volume determined by the sound characteristic determination unit 326 is 32 dB, the awakening information generation unit 323D adds 1 to the number of times of entry associated with the sound volume of 30 dB obtained by rounding off the sound volume determined by the sound characteristic determination unit 326 and the sleep state before the time point of entry.

On the other hand, in a case where the sleep state of the sleeper is determined to change to the awake state (YES in step S82), the awakening information generation unit 323D adds 1 to each of the number of times of entry and the number of times of awakening associated with the sleep state before the time point of entry and the sound volume determined by the sound characteristic determination unit 326 (step S85).

At this time, the awakening information generation unit 323D rounds off the sound volume determined by the sound characteristic determination unit 326, and adds 1 to each of the number of times of entry and the number of times of awakening associated with the rounded sound volume and the sleep state before the time point of entry. For example, if the sound volume determined by the sound characteristic determination unit 326 is 32 dB, the awakening information generation unit 323D adds 1 to each of the number of times of entry and the number of times of awakening associated with the sound volume of 30 dB obtained by rounding off the sound volume determined by the sound characteristic determination unit 326 and the sleep state before the time point of entry.

Next, the awakening information generation unit 323D calculates the awakening probability based on the number of times of entry and the number of times of awakening associated with the sleep state before the time point of entry and the sound volume determined by the sound characteristic determination unit 326 (step S86).

Next, the awakening information generation unit 323D stores the calculated awakening probability in the awakening information storage unit 331D in association with the sleep state before the time point of entry and the sound volume determined by the sound characteristic determination unit 326 (step S87).

Note that, since the awakening probability can be calculated from the number of times of entry and the number of times of awakening, the awakening information storage unit 331D may be configured to store only the number of times of entry and the number of times of awakening in association with the sleep state and the sound volume. In this case, the processing of steps S86 and S87 of FIG. 24 is not performed, and, in step S73 of FIG. 23, the awakening information generation unit 323D may calculate the awakening probability for each sound volume based on the number of times of entry and the number of times of awakening stored in the awakening information storage unit 331D.

Note that, in the fifth embodiment, the presentation control unit 324D generates the presentation screen information including the sleep state of the sleeper in the bedroom and the awakening probability of the sleeper for each sound volume as shown in FIG. 25. However, the present disclosure is not particularly limited to this. The presentation control unit 324D may generate presentation screen information including the number of times sleep continues and the number of times of awakening for each sound volume with respect to the sleep state of the sleeper in the bedroom.

FIG. 26 is a diagram showing a first variation of the presentation screen information displayed on the display device in the fifth embodiment.

In a case where the sleep state of the sleeper is determined to be the REM sleep state, the presentation control unit 324D refers to a table of the awakening information storage unit 331D, and specifies the number of times of entry and the number of times of awakening for each sound volume associated with the REM sleep state. Then, the presentation control unit 324D calculates the number of times obtained by subtracting the number of times of awakening from the number of times of entry as the number of times sleep continues, and generates presentation screen information that represents the number of times sleep continues and the number of times of awakening for each sound volume in a graph. The display unit 42 of the display device 4 displays the presentation screen information shown in FIG. 26. As shown in FIG. 26, the presentation screen information is a graph in which the horizontal axis represents the sound volume and the vertical axis represents the number of times, and includes the number of times sleep continues and the number of times of awakening for each sound volume associated with the sleep state of the sleeper in the bedroom.

Further, in the fifth embodiment, the presentation control unit 324D may present information based on the characteristic of the sound associated with the awakening information to be presented.

FIG. 27 is a diagram showing a second variation of the presentation screen information displayed on the display device in the fifth embodiment.

In a case where the sleep state of the sleeper is determined to be the REM sleep state, the presentation control unit 324D refers to a table of the awakening information storage unit 331D, and specifies the awakening probability of 0.25 associated with the REM sleep state. Further, the presentation control unit 324D specifies, as a recommended sound volume, the sound volume corresponding to the awakening probability of 50% or less among the awakening probabilities for sound volumes associated with the REM sleep state.

In this case, for example, the presentation control unit 324D specifies the sound volume of 40 dB corresponding to the awakening probability of 33% as the recommended sound volume. Then, the presentation control unit 324D generates presentation screen information indicating "Yamada in bedroom is in REM sleep state. If you enter the room now, probability of awakening Yamada is 25%. Sound lower than 40 dB is recommended". The display unit 42 of the display device 4 displays the presentation screen information shown in FIG. 27. As shown in FIG. 27, the presentation screen information presents the sleep state of the sleeper in the bedroom, the awakening probability of the sleeper, and the recommended sound volume.

Further, in the fifth embodiment, sound data in the bedroom when a person enters the bedroom is acquired, and the sound volume of the acquired sound data is associated with the awakening probability. However, the present disclosure is not particularly limited to this, and illuminance data in the bedroom when a person enters the bedroom may be acquired, and a characteristic of the acquired illuminance data may be associated with the awakening probability. In this case, the information presentation system includes an illuminance sensor that acquires illuminance data in the bedroom. The illuminance sensor acquires the illuminance data in the bedroom and transmits the acquired illuminance data to the server apparatus 3D.

Then, the communication unit 31D of the server apparatus 3D further includes an illuminance data receiving unit. The illuminance data receiving unit receives illuminance data transmitted by the illuminance sensor. The illuminance data receiving unit acquires illuminance data output from the illuminance sensor existing in the bedroom (space). The processor 32D further includes an illuminance characteristic determination unit. The illuminance characteristic determination unit uses the illuminance data and the room entry determination signal (detection data) to determine a characteristic of illuminance in the bedroom (space) within a predetermined time from a time point at which a person (object) is estimated to enter the bedroom (space). Note that the characteristic of the illuminance is, for example, illuminance. Further, the characteristic of the illuminance may be, for example, a color temperature.

The awakening information generation unit 323D associates the characteristic of the illuminance determined by the illuminance characteristic determination unit with the awakening information. Based on a result of the first determination by the awakening determination unit 322 and a determination result of the characteristic of the illuminance by the illuminance characteristic determination unit, the awakening information generation unit 323D generates, for each degree of illuminance (the characteristic of the illuminance), awakening information for determining the possibility of a person being awakened by the entry of a person (object) in a case where the person is in the sleep state before the time point of entry. The awakening information generation unit 323D further associates the awakening information for each degree of illuminance (the characteristic of the illuminance) with the sleep state before the time point of entry.

The awakening information storage unit 331D stores the illuminance, the number of times of entry, the number of times of awakening, and the awakening probability in association with each other for each sleep state. For example, for the REM sleep state, the awakening information storage unit 331D stores the illuminance of 0 lux, the number of times of entry of 18, the number of times of awakening of 0, and the awakening probability of 0 associated with each other, the illuminance of 10 lux, the number of times of entry of 13, the number of times of awakening of 0, and awakening probability of 0 associated with each other, the illuminance of 50 lux, the number of times of entry of 9, the number of times of awakening of 1, and the awakening probability of 0.11 associated with each other, the illuminance of 100 lux, the number of times of entry of 6, the number of times of awakening of 2, and the awakening probability of 0.33 associated with each other, the illuminance of 300 lux, the number of times of entry of 7, the number of times of awakening of 5, and the awakening probability of 0.71 associated with each other, and the illuminance of 500 lux, the number of times of entry of 12, the number of times of awakening of 11, and the awakening probability of 0.91 associated with each other. Note that the illuminance stored in the awakening information storage unit 331D is not limited to 0 lux, 10 lux, 50 lux, 100 lux, 300 lux, or 500 lux described above.

The presentation control unit 324D presents the awakening information and the characteristic of the illuminance associated with the awakening information. The presentation control unit 324D presents the awakening information corresponding to the characteristic of the illuminance.

FIG. 28 is a diagram showing a third variation of the presentation screen information displayed on the display device in the fifth embodiment.

In a case where the sleep state of the sleeper is determined to be the REM sleep state, the presentation control unit 324D refers to a table of the awakening information storage unit 331D, and specifies the awakening probability for each degree of illuminance associated with the REM sleep state. Then, the presentation control unit 324D generates presentation screen information indicating "Yamada in bedroom is in REM sleep state. If you enter the room now, Yamada will not be awakened by brightness of 0 to 10 lux. Probability of awakening Yamada is 11% with brightness of 50 lux. Probability of awakening Yamada is 33% with brightness of 100 lux. Probability of awakening Yamada is 71% with brightness of 300 lux. Probability of awakening Yamada is 91% with brightness of 500 lux". The display unit 42 of the display device 4 displays the presentation screen information shown in FIG. 28. As shown in FIG. 28, the presentation screen information presents the sleep state of the sleeper in the bedroom and the awakening probability of the sleeper for each degree of illuminance.

Further, the presentation control unit 324D may generate presentation screen information including the number of times sleep continues and the number of times of awakening for each degree of illuminance with respect to the sleep state of the sleeper in the bedroom.

FIG. 29 is a diagram showing a fourth variation of the presentation screen information displayed on the display device in the fifth embodiment.

In a case where the sleep state of the sleeper is determined to be the REM sleep state, the presentation control unit 324D refers to a table of the awakening information storage unit 331D, and specifies the number of times of entry and the number of times of awakening for each degree of illuminance associated with the REM sleep state. Then, the presentation control unit 324D calculates the number of times obtained by subtracting the number of times of awakening from the number of times of entry as the number of times sleep continues, and generates presentation screen information that represents the number of times sleep continues and the number of times of awakening for each degree of illuminance in a graph. The display unit 42 of the display device 4 displays the presentation screen information shown in FIG. 29. As shown in FIG. 29, the presentation screen information is a graph in which the horizontal axis represents the illuminance and the vertical axis represents the number of times, and includes the number of times sleep continues and the number of times of awakening for each degree of illuminance associated with the sleep state of the sleeper in the bedroom.

Further, in the fifth embodiment, the presentation control unit 324D may present information based on the characteristic of the illuminance associated with the awakening information to be presented.

FIG. 30 is a diagram showing a fifth variation of the presentation screen information displayed on the display device in the fifth embodiment.

In a case where the sleep state of the sleeper is determined to be the REM sleep state, the presentation control unit 324D refers to a table of the awakening information storage unit 331D, and specifies the awakening probability of 0.25 associated with the REM sleep state. Further, the presentation control unit 324D specifies, as a recommended illuminance, the degree of illuminance corresponding to the awakening probability of 50% or less among the awakening probabilities for degrees of illuminance associated with the REM sleep state. In this case, for example, the presentation control unit 324D specifies the illuminance of 100 lux corresponding to the awakening probability of 33% as the recommended illuminance. Then, the presentation control unit 324D generates presentation screen information indicating "Yamada in bedroom is in REM sleep state. If you enter the room now, probability of awakening Yamada is 25%. Brightness lower than 100 lux is recommended". The display unit 42 of the display device 4 displays the presentation screen information shown in FIG. 30. As shown in FIG. 30, the presentation screen information presents the sleep state of the sleeper in the bedroom, the awakening probability of the sleeper, and the recommended illuminance.

Sixth Embodiment

In the sixth embodiment, processing related to control of a home appliance installed in space is executed based on awakening information.

Figure 31:
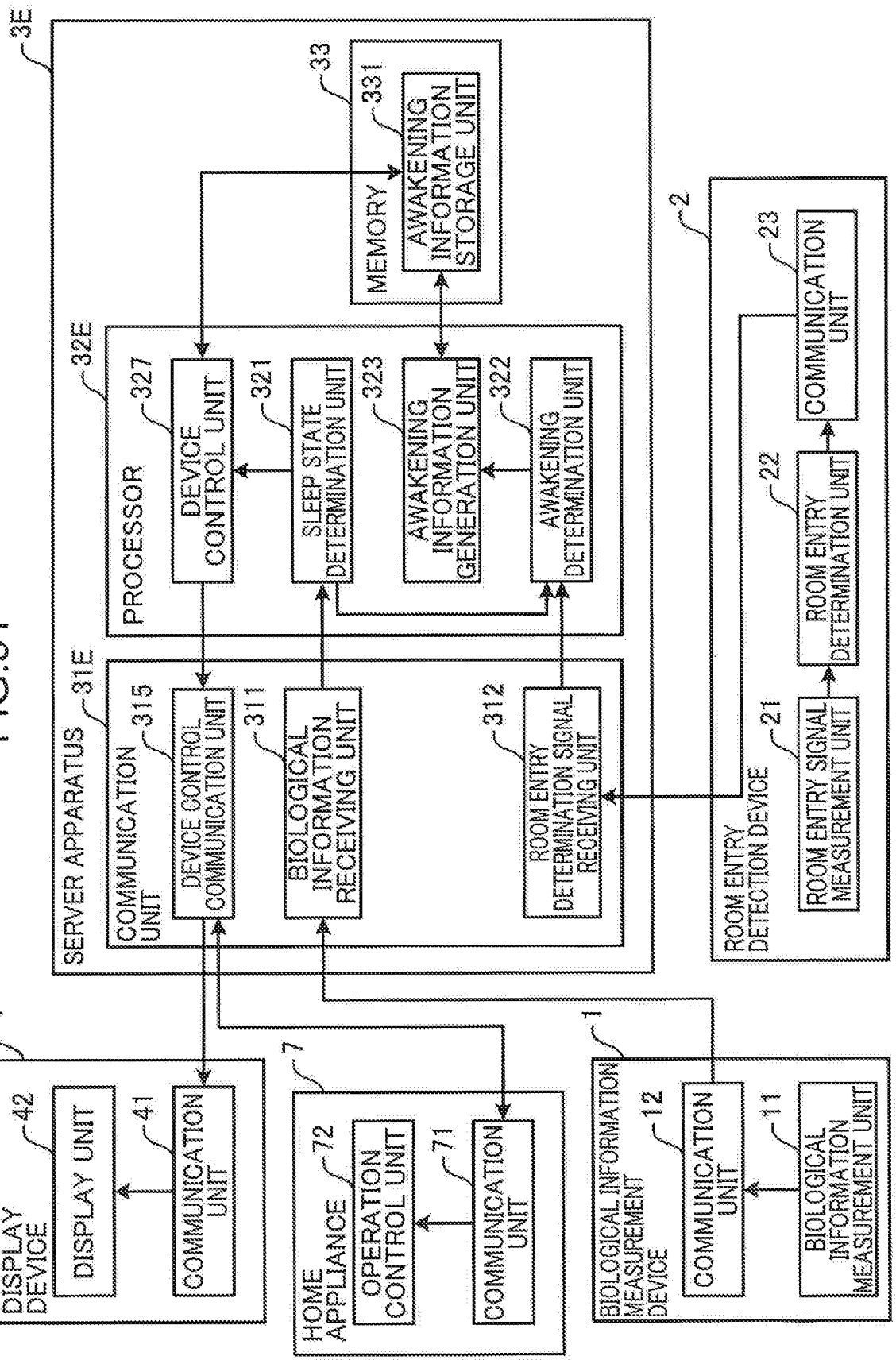
FIG. 31 is a block diagram showing a configuration of the information presentation system in a sixth embodiment of the present disclosure.

FIG. 31 is a block diagram showing a configuration of the information presentation system in the sixth embodiment of the present disclosure. In the sixth embodiment, the information presentation system further includes a home appliance 7. For example, the home appliance 7 is a lighting home appliance such as a ceiling light, a television receiver, a projector display home appliance, a sound output home appliance such as a music speaker or a smart speaker, or an air-conditioning home appliance. The air-conditioning home appliance is an air conditioner, an air cleaner, a humidifier, or the like.

The home appliance 7 includes a communication unit 71 and an operation control unit 72. The communication unit 71 receives a control instruction transmitted from a server apparatus 3E. The operation control unit 72 controls operation of the home appliance 7 based on the control instruction received by the communication unit 71.

The server apparatus 3E includes a device control communication unit 315 instead of the presentation screen information transmitting unit 313 of the first embodiment, and includes a device control unit 327 instead of the presentation control unit 324 of the first embodiment.

In addition to the function of the presentation screen information transmitting unit 313, the device control communication unit 315 transmits a control instruction for the home appliance 7 to the home appliance 7. The control instruction is generated by the device control unit 327.

In addition to the function of the presentation control unit 324, the device control unit 327 performs processing related to control of the home appliance 7. The device control unit 327 performs home appliance control processing for the home appliance 7 based on the awakening information. The home appliance control processing includes control of the home appliance 7. For example, in a case where the home appliance 7 is a lighting device, when the sleep state of the sleeper is determined to be the REM sleep state, the device control unit 327 refers to a table of the awakening information storage unit 331, and specifies the awakening probability associated with the REM sleep state. In a case where the awakening probability is equal to or greater than the threshold, the device control unit 327 generates control instruction information for lowering the illuminance below set illuminance.

Note that the device control unit 327 may generate the control instruction information based also on environment information associated with the awakening information. For example, in a case where the home appliance 7 is a lighting device and the environment information is illuminance, as in the fifth embodiment, when the sleep state of the sleeper is determined to be the REM sleep state, the device control unit 327 refers to a table of the awakening information storage unit 331, and specifies the awakening probability for each degree of illuminance associated with the REM sleep state. The device control unit 327 specifies illuminance at which the awakening probability is lower than the threshold. The device control unit 327 generates the control instruction information that causes the lighting device to output lighting at the specified illuminance.

Further, the device control unit 327 may generate presentation screen information for inquiring whether or not to control the home appliance 7 based on the awakening information. That is, the home appliance control processing includes inquiring whether or not to control the home appliance 7. For example, in a case where the sleep state is the REM sleep state and the illuminance with the awakening probability of less than the threshold of 25% is 100 lux, the device control unit 327 generates the control instruction information so that the illuminance becomes less than 100 lux for a ceiling light that is the home appliance 7. Then, the device control unit 327 generates presentation screen information indicating the content of the control instruction information as shown in FIG. 32.

Further, the device control unit 327 may generate presentation screen information for inquiring whether or not to control the home appliance 7 based on the awakening information. That is, the home appliance control processing includes presenting recommendation for controlling the home appliance 7. For example, in a case where the sleep state is the REM sleep state and the illuminance with the awakening probability of less than the threshold of 25% is 100 lux, the device control unit 327 generates the presentation screen information inquiring whether or not to control a ceiling light that is the home appliance 7 so that the illuminance becomes less than 100 lux as shown in FIG. 33. The device control unit 327 generates the control instruction information in a case where the response is YES, and does not generate the control instruction information in a case where the response is NO.

Further, the device control unit 327 may generate presentation screen information for recommending control of the home appliance 7 based on the awakening information. For example, in a case where the sleep state is the REM sleep state and the illuminance with the awakening probability of less than the threshold of 25% is 100 lux, the device control unit 327 generates the presentation screen information recommending the user to operate a ceiling light that is the home appliance 7 so that the illuminance becomes less than 100 lux as shown in FIG. 34. In this case, the device control unit 327 does not generate the control instruction information.

Note that the device control unit 327 may generate the presentation screen information including the awakening information as in other embodiments.

Figure 35:
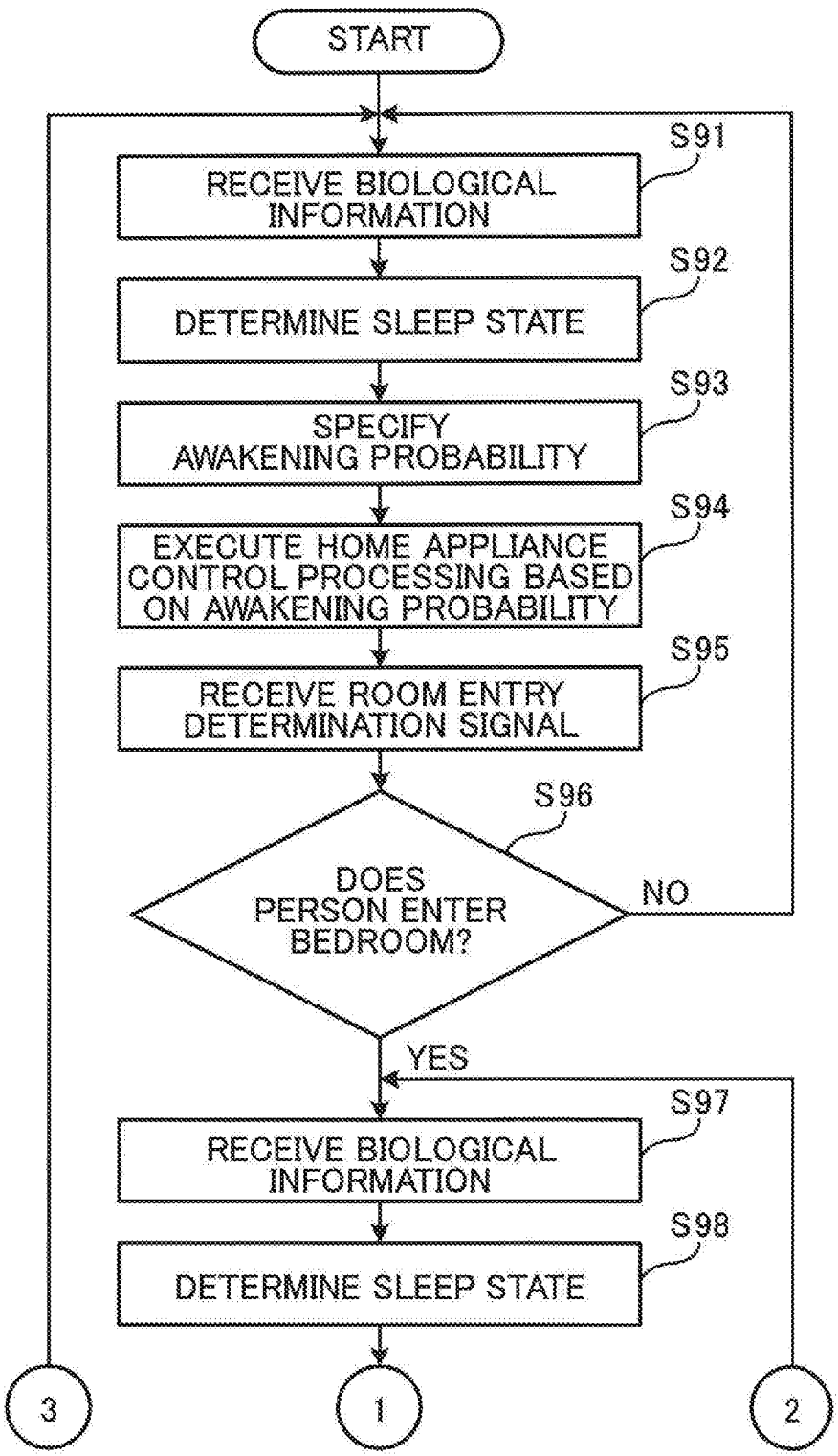
FIG. 35 is a first flowchart for describing operation of the server apparatus in the sixth embodiment of the present disclosure.

FIG. 35 is a first flowchart for describing operation of the server apparatus in the sixth embodiment of the present disclosure. Note that the second flowchart is the same as the second flowchart of the previous embodiments (for example, the first embodiment), and is therefore omitted.

First, processing of steps S91 to S93, which is the same as that of steps S1 to S3 in FIG. 5, is performed.

Next, the device control unit 327 executes home appliance control processing based on the specified awakening probability (step S94). Specifically, the device control unit 327 generates the control instruction information for controlling the home appliance 7 based on the sleep state determined based on the biological information and the awakening probability associated with the sleep state. Then, the device control communication unit 315 transmits the generated control instruction information to the home appliance 7. The home appliance 7 controls the operation of the home appliance 7 based on the received control instruction information.

The processing of step S95 and subsequent steps is the same as the processing of step S6 and subsequent steps in FIG. 5, and will be omitted from description.

As described above, in the sixth embodiment, the server apparatus 3E executes the home appliance control processing based on the awakening information associated with the sleep state. For this reason, when an object enters space, the home appliance 7 can control the environment in the space to be an environment in which the sleeper is unlikely to awaken. Therefore, even if an object enters the space, awakening of the sleeper can be suppressed.

Seventh Embodiment

In a seventh embodiment, an operation state of the home appliance 7 when a person enters the bedroom is acquired, and the acquired operation state is associated with the awakening information. Note that the configuration of the information presentation system of the seventh embodiment is the same as the configuration of the information presentation system of the sixth embodiment shown in FIG. 31. For this reason, the configuration of the information presentation system according to the seventh embodiment will be described with reference to FIG. 31.

The home appliance 7 transmits operation state information to the server apparatus 3E. Specifically, the operation control unit 72 generates the operation state information when controlling the operation of the home appliance 7. The communication unit 71 transmits the operation state information generated by the operation control unit 72 to the server apparatus 3E. The operation state information may be transmitted every time the information is generated, or may be transmitted collectively on a regular basis.

The device control communication unit 315 receives the operation state information transmitted from the home appliance 7.

The device control unit 327 determines an operation state of the home appliance 7 within a predetermined time from a time point at which a person is estimated to enter the bedroom based on the operation state information and the room entry determination signal.

The awakening information generation unit 323 associates the determined operation state with the awakening information. Based on a result of the first determination by the awakening determination unit 322 and a determination result of the operation state by the device control unit 327, the awakening information generation unit 323 generates, for each operation state, awakening information for determining the possibility of a sleeper being awakened by the entry of a person in a case where the sleeper is in the sleep state before the time point of entry. The awakening information generation unit 323 further associates the awakening information for each operation state with the sleep state before the time point of entry.

For example, the awakening information generation unit 323 counts, for each operation state, a combination of the number of times of entry indicating the number of times another person enters a room while a sleeper is sleeping, and the number of times of awakening indicating the number of times a sleep state of the sleeper changes to awakening within a predetermined time from the time point of entry at which the other person is estimated to enter the bedroom 111, and generates the awakening probability by dividing the number of times of awakening by the number of times of entry in association with the sleep state before the time point of entry for each operation state.

The awakening information storage unit 331 stores the number of times of entry, the number of times of awakening, and the awakening probability in association with the sleep state for each operation state of the home appliance 7.

The device control unit 327 specifies the awakening information for each operation state based on the sleep state. The device control unit 327 specifies an operation state in which the awakening probability is lower than the threshold. The device control unit 327 generates the control instruction information so that the home appliance 7 operates in the specified operation state.

Figure 36:
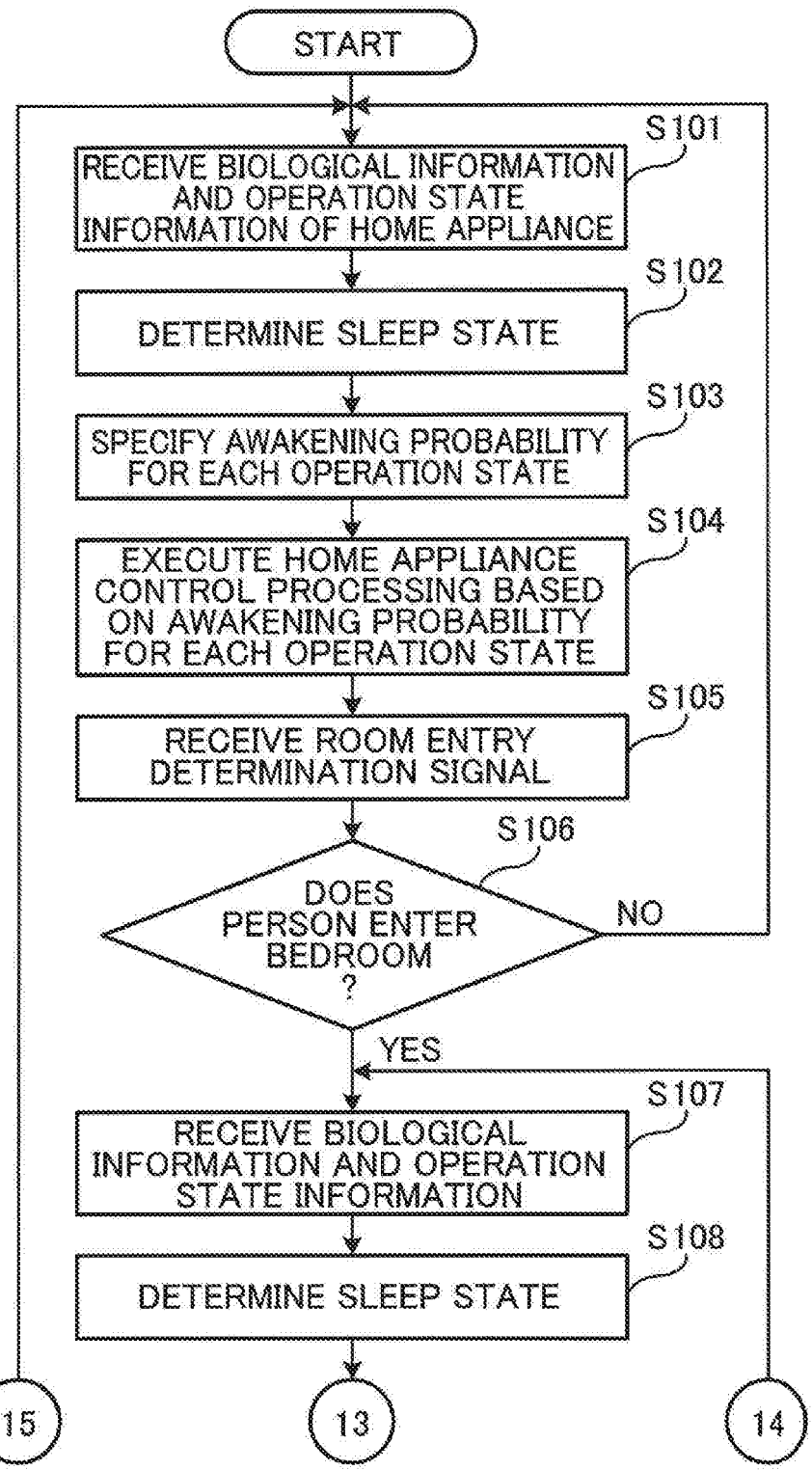
FIG. 36 is a first flowchart for describing operation of the server apparatus in the seventh embodiment of the present disclosure.

FIG. 36 is a first flowchart for describing operation of the server apparatus according to the seventh embodiment of the present disclosure. FIG. 37 is a second flowchart for describing the operation of the server apparatus according to the seventh embodiment of the present disclosure.

Note that the processing in steps S102, S105, S106, and S108 shown in FIG. 36 is the same as the processing in steps S2, S6, S7, and S9 shown in FIG. 5, and will be omitted from description. Further, the processing in steps S109, S110, S113, and S114 shown in FIG. 37 is the same as the processing in steps S10, S11, S14, and S15 shown in FIG. 6, and will be omitted from description.

First, the biological information receiving unit 311 receives biological information from the biological information measurement device 1, and the device control communication unit 315 receives the operation state information from the home appliance 7 (step S101).

After determining the sleep state in step S102, the device control unit 327 refers to the awakening information storage unit 331 to specify, for each operation state, the awakening probability associated with the sleep state determined by the sleep state determination unit 321 (step S103). The awakening information storage unit 331 stores the operation state, the number of times of entry, the number of times of awakening, and the awakening probability in association with each other for each sleep state.

For example, for the REM sleep state, the awakening information storage unit 331 stores a state in which light of 100 lux is output, the number of times of entry of 6, the number of times of awakening of 2, and the awakening probability of 0.33 in association with each other.

Next, the device control unit 327 executes the home appliance control processing based on the specified awakening probability for each operation state (step S104). Specifically, the device control unit 327 specifies an operation state in which the awakening probability is lower than the threshold. The device control unit 327 generates the control instruction information for controlling the home appliance 7 to operate in the specified operation state. The device control communication unit 315 transmits the control instruction information generated by the device control unit 327 to the home appliance 7. The home appliance 7 causes the home appliance 7 to make transition to the operation state instructed based on the received control instruction information.

When a person is determined to enter the bedroom in steps S105 and S106, the biological information and the operation state information are received as in step S101 (step S107).

Next, in FIG. 37, in a case where a predetermined time is determined to have elapsed since the time point of entry at which the person is determined to enter the bedroom (YES in step S110), the awakening information generation unit 323 adds 1 to the number of times of entry associated with the sleep state before the time point of entry and the operation state of the home appliance 7 (step S111).

On the other hand, in a case where the sleep state of the sleeper is determined to change to the awake state (YES in step S109), the awakening information generation unit 323 adds 1 to each of the number of times of entry and the number of times of awakening associated with the sleep state before the time point of entry and the operation state of the home appliance 7 (step S112).

Thereafter, the awakening probability is calculated based on the number of times of entry and the number of times of awakening (step S113), and the calculated awakening probability is stored in the awakening information storage unit 331 in association with the sleep state before the time point of entry and the operation state of the home appliance 7 (step S114).

As described above, in the seventh embodiment, the server apparatus 3E acquires the operation state of the home appliance 7, generates, in association with the sleep state before a time point at which an object is estimated to enter space and the operation state, the awakening information for determining the possibility that a person is awakened by the entry of the object in the sleep state before the time point and the operation state based on a result of the first determination, and executes the home appliance control processing based on the awakening information. For this reason, an environment in which a sleeper is unlikely to awaken when an object enters space can be provided without a sensor for sensing the environment of the space.

(Variation)

Note that, in each of the above embodiments, the timing of presenting presentation information, such as the awakening information, and the timing of controlling the home appliance 7 are optional. However, the presentation information may be presented at a specific timing. Specifically, the server apparatus 3E acquires a position of an object, and determines the timing of executing the home appliance control processing or the timing of presenting the awakening information based on a positional relationship between the position of the object and space. For example, the device control communication unit 315 acquires positional information of a person and a room. The device control unit 327 calculates a distance between the person and the room based on the position information acquired by the device control communication unit 315. In a case where the calculated distance is equal to or less than the threshold, the device control unit 327 generates the control instruction information for controlling the home appliance 7, or generates the presentation screen information, such as the awakening information or an inquiry for control execution. For this reason, unnecessary control and presentation can be reduced as the home appliance 7 is controlled or the presentation information is presented at a timing at which the possibility that a person enters the room becomes high. In other words, a processing amount of the server apparatus 3E and a communication amount of a network can be reduced.

Further, the awakening information generation unit 323 may also generate the awakening information by using a trained model obtained by machine learning of a model in which the sleep state before the time point of entry and the sleep state within a predetermined time from the time point of entry are used as teacher data (that is, training data). For example, the model may be a model that solves a classification problem of the sleep state within a predetermined time from the time point of entry.

The processor 32 of the server apparatus 3 may further include a training unit that generates a trained model by executing machine learning for a model so as to input of the sleep state before the time point of entry and output a sleep state within a predetermined time from an estimated time point of entry. The awakening information generation unit 323 may acquire the sleep state within a predetermined time from the time point of entry by inputting the sleep state output from the sleep state determination unit 321 to the trained model. Then, the awakening information generation unit 323 may provide the likelihood of awakening in the acquired sleep state to the presentation control unit 324 as the awakening probability (that is, the awakening information). Note that the trained model may be designed to output the likelihood of each sleep state (that is, the probability of transition to each sleep state).

Note that machine learning may be used for sleep determination processing of the sleep state determination unit 321, awakening determination processing of the awakening determination unit 322, awakening information generation processing of the awakening information generation unit 323, and sound characteristic determination processing of the sound characteristic determination unit 326. Examples of the machine learning include supervised learning for learning a relationship between input and output using supervised data in which a label (output information) is provided to input information, unsupervised learning for building a structure of data only from unlabeled input, semi-supervised learning that handles both labeled and unlabeled inputs, and reinforcement learning for learning continuous actions that can obtain a largest reward by obtaining a feedback (reward) for an action selected from an observation result of a state. Further, as a specific method of machine learning, there exist a neural network (including deep learning using a multilayer neural network), genetic programming, a decision tree, a Bayesian network, a support vector machine (SVM), and the like. In the present disclosure, any of the specific examples described above may be used.

Note that, in each of the above embodiments, each constituent may be configured by dedicated hardware or may be realized by executing a software program suitable for each constituent. Each constituent may be realized by a program execution unit, such as a CPU or a processor, reading and executing a software program recorded on a recording medium, such as a hard disk or a semiconductor memory.

Part or all of functions of the device according to the embodiments of the present disclosure are typically realized as large scale integration (LSI) that is an integrated circuit. These may be individually made into one chip, or may be made into one chip so as to include part or all of them. Further, the circuit integration is not limited to LSI, and may be realized by a dedicated circuit or a general-purpose processor. A field programmable gate array (FPGA) that can be programmed after manufacture of the LSI or a reconfigurable processor that can reconfigure connection and setting of circuit cells inside the LSI may be used.

Further, part or all of the functions of the device according to the embodiments of the present disclosure may be realized by a processor, such as a CPU, executing a program.

Further, all the numbers used above are illustrated for specifically describing the present disclosure, and the present disclosure is not limited to the illustrated numbers.

Further, the order in which the steps shown in the flowcharts are executed is for specifically illustrating the present disclosure, and may be the order other than the above as long as a similar effect can be obtained. Further, part of the above steps may be executed simultaneously (in parallel) with other steps.

The information processing method and the information processing system according to the present disclosure, which can control the entry of an object into space where a sleeper is present in accordance with the ease of awakening of each individual sleeper, are useful as an information processing method and an information processing system for presenting information according to a sleep state of a person existing in the space.

This application is based on Japanese Patent application No. 2019-033142 filed in Japan Patent Office on Feb. 26, 2019 and Japanese Patent application No. 2019-184638 filed in Japan Patent Office on Oct. 7, 2019, the contents of which are hereby incorporated by reference.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

The invention claimed is:

1. An information processing method executed by a computer, the information processing method comprising:
acquiring a sleep state of a person existing in space;
acquiring detection data output from a sensor that detects entry of an object into the space;
performing a first determination to determine whether or not the sleep state changes to awakening within a predetermined time from a time point at which the object is estimated to enter the space based on the sleep state and the detection data;
generating, in association with the sleep state before the time point, awakening information for determining possibility that the person is awakened by entry of the object in a case where the person is in the sleep state before the time point based on a result of the first determination; and
presenting the awakening information associated with the sleep state via a presentation device.

2. The information processing method according to claim 1, wherein
the presenting the awakening information includes presenting the awakening information in a case where the sleep state is not awakening.

3. The information processing method according to claim 1, further comprising
performing a second determination to determine transition of a sleep state after the sleep state changes to awakening based on the sleep state,
wherein the generating the awakening information includes generating the awakening information based on a result of the first determination and a result of the second determination.

4. The information processing method according to claim 3, wherein
the generating the awakening information includes generating the awakening information based on whether or not transition is determined to be made in the sleep state from awakening to another state in the second determination.

5. The information processing method according to claim 3, wherein
the generating the awakening information includes generating the awakening information based on an elapsed time from a time point at which the sleep state changes to awakening to a time point at which transition is determined to be made in the sleep state from awakening to the another state in the second determination.

6. The information processing method according to claim 1, wherein
the generating the awakening information includes calculating possibility of awakening of the person based on a result of the first determination, and generating the calculated possibility of awakening as the awakening information.

7. The information processing method according to claim 1, further comprising:
acquiring sound data output from a microphone existing in the space; and
determining a characteristic of a sound within the space within a predetermined time from a time point at which the object is estimated to enter the space based on the sound data and the detection data,
wherein the generating the awakening information includes associating the determined characteristic of the sound with the awakening information, and
the presenting the awakening information includes presenting the awakening information and the characteristic of the sound associated with the awakening information.

8. The information processing method according to claim 7, wherein
the presenting the awakening information includes presenting the awakening information corresponding to the characteristic of the sound.

9. The information processing method according to claim 7, wherein
the presenting the awakening information includes presenting information based on the characteristic of the sound associated with the awakening information to be presented.

10. The information processing method according to claim 1, further comprising:
acquiring illuminance data output from an illuminance sensor existing in the space; and determining a characteristic of an illuminance within the space within a predetermined time from a time point at which the object is estimated to enter the space based on the illuminance data and the detection data, wherein the generating the awakening information includes associating the determined characteristic of the illuminance with the awakening information, and the presenting the awakening information includes presenting the awakening information and the characteristic of the illuminance associated with the awakening information.

11. The information processing method according to claim 10, wherein the presenting the awakening information includes presenting the awakening information corresponding to the characteristic of the illuminance.

12. The information processing method according to claim 11, wherein the presenting the awakening information includes presenting information based on the characteristic of the illuminance associated with the awakening information to be presented.

13. An information processing system comprising:

an information processing device;

a sensor that detects entry of an object into space; and a presentation device, wherein the information processing device includes:

a sleep state acquisition unit that acquires a sleep state of a person existing in the space;

a detection data acquisition unit that acquires detection data output from the sensor, a determination unit that performs a first determination to determine whether or not the sleep state changes to awakening within a predetermined time from a time point at which the object is estimated to enter the space based on the sleep state and the detection data;

a generation unit that generates, in association with the sleep state before the time point, awakening information for determining possibility that the person is awakened by entry of the object in a case where the person is in the sleep state before the time point based on a result of the first determination; and a presentation unit that presents the awakening information associated with the sleep state via the presentation device.

14. An information processing method executed by a computer, the information processing method comprising:

acquiring a sleep state of a person existing in space;

acquiring detection data output from a sensor that detects entry of an object into the space;

performing a first determination to determine whether or not the sleep state changes to awakening within a predetermined time from a time point at which the object is estimated to enter the space based on the sleep state and the detection data;

generating, in association with the sleep state before the time point, awakening information for determining possibility that the person is awakened by entry of the object in a case where the person is in the sleep state before the time point based on a result of the first determination; and executing, based on the awakening information associated with the sleep state, home appliance control processing that is at least one of controlling a home appliance in the space, inquiring whether or not to control the home appliance via a presentation device, and presenting recommendation for controlling the home appliance via the presentation device.

15. The information processing method according to claim 14, further comprising presenting the awakening information via the presentation device.

16. The information processing method according to claim 14, further comprising:

acquiring a position of the object; and determining a timing of executing the home appliance control processing or a timing of presenting the awakening information based on a positional relationship between the position of the object and the space.

17. The information processing method according to claim 14, further comprising:

acquiring an operation state of the home appliance;

generating, in association with the sleep state before the time point and the operation state, awakening information for determining possibility that the person is awakened by entry of the object in a case where the person is in the sleep state before the time point and the operation state based on a result of the first determination; and executing the home appliance control processing based on the awakening information associated with the sleep state and the operation state.

* * * * *